United States Patent
Sekiguchi et al.

(10) Patent No.: US 10,287,541 B2
(45) Date of Patent: May 14, 2019

(54) CELL CULTURE VESSEL COATED WITH LAMININ FRAGMENT IN DRY STATE

(71) Applicant: OSAKA UNIVERSITY, Osaka (JP)

(72) Inventors: Kiyotoshi Sekiguchi, Osaka (JP); Ko Tsutsui, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 361 days.

(21) Appl. No.: 14/897,298

(22) PCT Filed: May 9, 2014

(86) PCT No.: PCT/JP2014/062449
§ 371 (c)(1),
(2) Date: Jan. 21, 2016

(87) PCT Pub. No.: WO2014/199754
PCT Pub. Date: Dec. 18, 2014

(65) Prior Publication Data
US 2016/0137965 A1  May 19, 2016

(30) Foreign Application Priority Data

Jun. 12, 2013  (JP) ................................ 2013-123554

(51) Int. Cl.
| | | |
|---|---|---|
| C12M 1/00 | (2006.01) | |
| C12M 1/12 | (2006.01) | |
| C12N 5/00 | (2006.01) | |
| C12N 9/10 | (2006.01) | |
| C07K 14/78 | (2006.01) | |
| C07K 14/79 | (2006.01) | |
| C07K 14/435 | (2006.01) | |
| C07K 14/765 | (2006.01) | |

(52) U.S. Cl.
CPC ........... *C12M 25/06* (2013.01); *C07K 14/435* (2013.01); *C07K 14/765* (2013.01); *C07K 14/78* (2013.01); *C07K 14/79* (2013.01); *C12M 23/20* (2013.01); *C12N 5/0068* (2013.01); *C12N 9/1088* (2013.01); *C12N 2533/00* (2013.01); *C12N 2533/52* (2013.01); *C12Y 205/01018* (2013.01)

(58) Field of Classification Search
CPC ..... C12M 25/06; C12M 23/20; C07K 14/435; C07K 14/765; C07K 14/78; C07K 14/79; C12N 5/0068; C12N 9/1088; C12N 2533/00; C12N 2533/52; C12Y 205/01018
USPC ....................................................... 435/325
See application file for complete search history.

(56) References Cited

U.S. PATENT DOCUMENTS

2007/0269886 A1  11/2007  Qian et al.
2008/0220516 A1  9/2008  Eddington et al.
2012/0220031 A1  8/2012  Sekiguchi et al.
2013/0280750 A1* 10/2013  Tryggvason ......... C12N 5/0676
                                                    435/29
2015/0065389 A1  3/2015  Eddington et al.

FOREIGN PATENT DOCUMENTS

| CN | 101182464 | 5/2008 | | |
|---|---|---|---|---|
| JP | 6-98757 | 4/1994 | | |
| JP | 8-173144 | 7/1996 | | |
| JP | 2011-78370 | 4/2011 | | |
| JP | 2011-79795 | 4/2011 | | |
| JP | WO 2013/047763 | * | 4/2013 | .............. C12M 3/00 |
| WO | 2008/060382 | 5/2008 | | |
| WO | 2011/043405 | 4/2011 | | |
| WO | 2013/047763 | 4/2013 | | |

OTHER PUBLICATIONS

International Search Report dated Aug. 12, 2014 in International (PCT) Application No. PCT/JP2014/062449.
English translation of International Preliminary Report on Patentability dated Dec. 12, 2015 in International (PCT) Application No. PCT/JP2014/062449.
Miyazaki et al., "Laminin E8 Fragments support efficient adhesion and expansion of dissociated human pluripotent stem cells", Nature Communications, vol. 3, No. 1236, Dec. 2012, pp. 1-10.
Miyazaki et al., "Recombinant human laminin isoforms can support the undifferentiated growth of human embryonic stem cells", Biochemical and Biophysical Research Communications, vol. 375, 2008, pp. 27-32.
Nishiuchi et al., "Ligand-binding specificities of laminin-binding integrins: A comprehensive survey of laminin-integrin interactions using recombinant α3β1, α7β1, and α6β4 integrins", Matrix Biology, vol. 25, 2006, pp. 189-197.

(Continued)

*Primary Examiner* — Jennifer M. H. Tichy
(74) *Attorney, Agent, or Firm* — Wenderoth, Lind & Ponack, L.L.P.

(57) ABSTRACT

Provided is a cell culture vessel characterized in that a surface to be in contact with cells is coated with a laminin fragment having integrin α6β1 binding activity or a modified form thereof in a dry state,
  the laminin fragment being derived from at least one kind selected from laminin α5β1γ1 and laminin α5β2γ1,
  the cell culture vessel being any of the following:
(1) a cell culture vessel of which a surface to be in contact with cells is coated only with a laminin fragment having integrin α6β1 binding activity or a modified form thereof in a dry state;
(2) a cell culture vessel of which a surface to be in contact with cells is coated with a laminin fragment having integrin α6β1 binding activity or a modified form thereof in combination with a laminin fragment having no integrin α6β1 binding activity in a dry state; and
(3) a cell culture vessel of which a surface to be in contact with cells is coated with a laminin fragment having integrin α6β1 binding activity or a modified form thereof in combination with a protein that is neither a laminin nor a laminin fragment, in a dry state.

6 Claims, 6 Drawing Sheets

Specification includes a Sequence Listing.

(56) References Cited

OTHER PUBLICATIONS

Ido et al., "The Requirement of the Glutamic Acid Residue at the Third Position from the Carboxyl Termini of the Laminin γ Chains in Integrin Binding by Laminins", The Journal of Biological Chemistry, vol. 282, No. 15, Apr. 13, 2007, pp. 11144-11154.

Taniguchi et al., "The C-terminal Region of Laminin β Chains Modulates the Integrin Binding Affinities of Laminins", The Journal of Biological Chemistry, vol. 284, No. 12, Mar. 20, 2009, pp. 7820-7831.

Doi et al., "Recombinant Human Laminin-10 (α5β1γ1) Production, Purification, and Migration-Promoting Activity on Vascular Endothelial Cells", The Journal of Biological Chemistry, vol. 277, No. 15, Apr. 12, 2002, pp. 12741-12748.

Extended European Search Report dated Jan. 3, 2017 in corresponding European Application No. 14811174.3.

\* cited by examiner

CELL CULTURE VESSEL COATED WITH LAMININ FRAGMENT IN DRY STATE

TECHNICAL FIELD

The present invention relates to a cell culture vessel, more particularly a cell culture vessel which is coated with a laminin fragment having integrin α6β1 binding activity or a modified form thereof in a dry state.

BACKGROUND ART

Human pluripotent stem cells, such as human ES cells and human iPS cells, are receiving worldwide attention for their potential application to regenerative medicine. The requirement for the application of human pluripotent stem cells to regenerative medicine is to develop techniques for culturing and propagating such stem cells in a safe and stable manner. In particular, the development of a method for stably culturing such stem cells under the conditions in which no feeder cells are used and no xenogeneic components are contained in the culture system (xeno-free) is a pressing issue.

The present inventors found that early embryonic pluripotent stem cells utilize, as their scaffold, basement membranes containing laminin α5β1γ1 (laminin 511) as a major component, and first in the world, reported that a recombinant protein of human laminin 511 is a useful feeder-free culture matrix for human ES cells (see Non Patent Literature 1). In addition, the present inventors also reported that laminin 511 has very high affinity for α6β1 integrin and that a laminin 511E8 fragment (laminin 511E8) is comparable in α6β1 integrin binding activity to a full-length laminin 511 (see Non Patent Literature 2). Furthermore, the present inventors found that pluripotent stem cells in a dissociated single-cell state can be passaged on laminin 511E8, although such dissociated single-cell culture had been conventionally difficult, and reported that human laminin 511E8 is very effective as a feeder-free culture matrix for human pluripotent stem cells (see Patent Literature 1 and Non Patent Literature 3).

For cell culture using human laminin 511E8 as a matrix, the surface of a culture vessel should be coated with the human laminin 511E8 in advance. For human pluripotent stem cell culture, such coating is performed by adding a human laminin 511E8 solution onto a culture vessel at a final concentration of 0.25 to 2.0 μg/cm$^2$ and incubating the culture vessel at 4° C. overnight or at room temperature up to 37° C. for 1 to 3 hours. However, laminins or their active fragments applied to coat the surface of the culture vessel are prone to inactivation by drying (see Non Patent Literature 4), and indeed, the present inventors confirmed that human laminin 511E8 applied to coat the surface of the culture vessel gradually became inactive after exposed to drying. Therefore, wider application of human laminin 511E8 as a culture matrix for human pluripotent stem cells in regenerative medicine etc. requires the development of a technology allowing the human laminin 511E8 applied as a coating component onto the surface of the culture vessel to be stably active in a dry state for a long period of time.

CITATION LIST

Patent Literature

Patent Literature 1: WO 2011/043405

Non Patent Literature

Non Patent Literature 1:
Miyazaki T, Futaki S, Hasegawa K, Kawasaki M, Sanzen N, Hayashi M, Kawase E, Sekiguchi K, Nakatsuji N, Suemori H. Recombinant human laminin isoforms can support the undifferentiated growth of human embryonic stem cells. Biochem. Biophys. Res. Commun. 375: 27-35, 2008.

Non Patent Literature 2:
Taniguchi Y, Ido H, Sanzen N, Hayashi M, Sato-Nishiuchi R, Futaki S, Sekiguchi K. The C-terminal region of laminin β chains modulates the integrin binding affinities of laminins. J Biol Chem. 284: 7820-7831, 2009.

Non Patent Literature 3:
Miyazaki T, Futaki S, Suemori H, Taniguchi Y, Yamada M, Kawasaki M, Hayashi M, Kumagai H, Nakatsuji N, Sekiguchi K, Kawase E. Laminin E8 fragments support efficient adhesion and expansion of dissociated human pluripotent stem cells. Nat Commun. 3:1236. Doi: 10.1038/ncomms2231, 2012.

Non Patent Literature 4:
Doi T, Thyboll J, Kortesmaa J, Jansson K, Iivanainen A, Parvardeh M, Timpl R, Hedin U, Swedenborg j, Tryggvason K. Recombinant human laminin-10 (α5β1γ1). J Biol Chem, 277, 12741-12748, 2002.

SUMMARY OF INVENTION

Technical Problem

An object of the present invention is to find a technology allowing a laminin fragment usable as a feeder-free culture matrix for human stem cells to be stably active in a dry state for a long period of time, and to provide a cell culture vessel coated with such a laminin fragment being active in a dry state.

Solution to Problem

In order to achieve the above-mentioned object, the present invention includes the following.
[1] A cell culture vessel characterized in that a surface to be in contact with cells is coated with a laminin fragment having integrin α6β1 binding activity or a modified form thereof in a dry state,
the laminin fragment being derived from at least one kind selected from laminin α5β1γ1 and laminin α5β2γ1,
the cell culture vessel being any of the following:
(1) a cell culture vessel of which a surface to be in contact with cells is coated only with a laminin fragment having integrin α6β1 binding activity or a modified form thereof in a dry state;
(2) a cell culture vessel of which a surface to be in contact with cells is coated with a laminin fragment having integrin α6β1 binding activity or a modified form thereof in combination with a laminin fragment having no integrin α6β1 binding activity in a dry state; and
(3) a cell culture vessel of which a surface to be in contact with cells is coated with a laminin fragment having integrin α6β1 binding activity or a modified form thereof in combination with a protein that is neither a laminin nor a laminin fragment, in a dry state.
[2] The cell culture vessel according to the above [1], wherein the coating concentration of the laminin fragment having integrin α6β1 binding activity or a modified form thereof in the above (1) is 0.7 μg/cm$^2$ or higher.
[3] The cell culture vessel according to the above [1], wherein, in the above (2), the coating concentration of the laminin fragment having integrin α6β1 binding activity or a modified form thereof is 1.5 µg/cm$^2$ or lower, and the coating concentration of the laminin fragment having no integrin α6β1 binding activity is 3 times or more that of the laminin fragment having integrin α6β1 binding activity or a modified form thereof.

[4] The cell culture vessel according to the above [1], wherein, in the above (3), the coating concentration of the laminin fragment having integrin α6β1 binding activity or a modified form thereof is 1.5 µg/cm$^2$ or lower, and the coating concentration of the protein that is neither a laminin nor a laminin fragment is 20 times or more that of the laminin fragment having integrin α6β1 binding activity or a modified form thereof.

[5] The cell culture vessel according to the above [1], wherein the laminin fragment is a laminin E8 fragment.

[6] The cell culture vessel according to the above [1], wherein the laminin fragment having no integrin α6β1 binding activity is a laminin α2β1γ1 fragment.

[7] The cell culture vessel according to the above [1], wherein the protein that is neither a laminin nor a laminin fragment is one or more kinds selected from the group consisting of gelatin, human serum albumin, bovine serum albumin, transferrin, myelin basic protein, β-lactoglobulin, glutathione S-transferase and collagen.

[8] The cell culture vessel according to any one of the above [1] to [7], wherein the cell culture vessel is produced through the steps of coating the surface to be in contact with cells with the desired protein(s) and subsequently drying the protein(s).

[9] A method for producing a cell culture vessel of which a surface to be in contact with cells is coated with a laminin fragment having integrin α6β1 binding activity or a modified form thereof in a dry state,
the laminin fragment being derived from at least one kind selected from laminin α5β1γ1 and laminin α5β2γ1,
the method comprising the steps of:
(A) preparing a coating solution containing a protein(s) to be used as a coating component(s),
(B) coating the surface to be in contact with cells with the desired protein(s), and
(C) drying the protein(s) applied in the coating step.

[10] A method for culturing mammalian cells, characterized by using the cell culture vessel according to any one of the above [1] to [8].

[11] The method according to the above [10], wherein the mammalian cells are ES cells, iPS cells, somatic stem cells or cells differentiated therefrom.

[12] A suppressor capable of preventing drying-caused reduction of the integrin α6β1 binding activity of a laminin fragment having integrin α6β1 binding activity or a modified form thereof,
the suppressor comprising, as an active ingredient, one or more kinds selected from the group consisting of gelatin, human serum albumin, bovine serum albumin, transferrin, myelin basic protein, β-lactoglobulin, glutathione S-transferase, collagen and a laminin α2β1γ1 E8 fragment.

[13] The method according to the above [9], wherein the protein(s) to be used as a coating component(s) is only the laminin fragment having integrin α6β1 binding activity or a modified form thereof, and the coating concentration of the laminin fragment having integrin α6β1 binding activity or a modified form thereof is 0.7 µg/cm$^2$ or higher.

[14] The method according to the above [9], wherein the protein(s) to be used as a coating component(s) are the laminin fragment having integrin α6β1 binding activity or a modified form thereof and a laminin fragment having no integrin α6β1 binding activity, the coating concentration of the laminin fragment having integrin α6β1 binding activity or a modified form thereof is 1.5 µg/cm$^2$ or lower, and the coating concentration of the laminin fragment having no integrin α6β1 binding activity is 3 times or more that of the laminin fragment having integrin α6β1 binding activity or a modified form thereof.

[15] The method according to the above [9], wherein the protein(s) to be used as a coating component(s) are the laminin fragment having integrin α6β1 binding activity or a modified form thereof and a protein that is neither a laminin nor a laminin fragment, the coating concentration of the laminin fragment having integrin α6β1 binding activity or a modified form thereof is 1.5 µg/cm$^2$ or lower, and the coating concentration of the protein that is neither a laminin nor a laminin fragment is 20 times or more that of the laminin fragment having integrin α6β1 binding activity or a modified form thereof.

[16] The method according to the above [9], wherein the laminin fragment is a laminin E8 fragment.

[17] The method according to the above [9], wherein the laminin fragment having no integrin α6β1 binding activity is a laminin α2β1γ1 fragment.

[18] The method according to the above [9], wherein the protein that is neither a laminin nor a laminin fragment is one or more kinds selected from the group consisting of gelatin, human serum albumin, bovine serum albumin, transferrin, myelin basic protein, β-lactoglobulin, glutathione S-transferase and collagen.

[19] The suppressor according to the above [12], wherein the laminin fragment having integrin α6β1 binding activity is derived from at least one kind selected from laminin α5β1γ1 and laminin α5β2γ1.

[20] The suppressor according to the above [12] or [19], wherein the laminin fragment is a laminin E8 fragment.

Hereinafter, laminin α5β1γ1 is referred to as "laminin 511", laminin α5β2γ1 is referred to as "laminin 521", and laminin α2β1γ1 is referred to as "laminin 211". Other laminins are similarly abbreviated. A laminin E8 fragment is referred to as "laminin E8", and an E8 fragment is referred to simply as "E8".

Advantageous Effects of Invention

The present invention can provide a cell culture vessel coated with a laminin fragment in a dry state, which fragment has integrin α6β1 binding activity and is usable as a feeder-free culture matrix for human pluripotent stem cells; a method for producing the cell culture vessel; and a method for culturing mammalian cells using the cell culture vessel. In addition, the present invention can provide a suppressor capable of preventing drying-caused reduction in the integrin α6β1 binding activity of a laminin fragment having such binding activity. The cell culture vessel of the present invention can be stored for a long period of time after its production, and even after its long-term storage, can be desirably used for feeder-free stem cell culture.

DESCRIPTION OF EMBODIMENTS

Cell Culture Vessel

Figure 1:
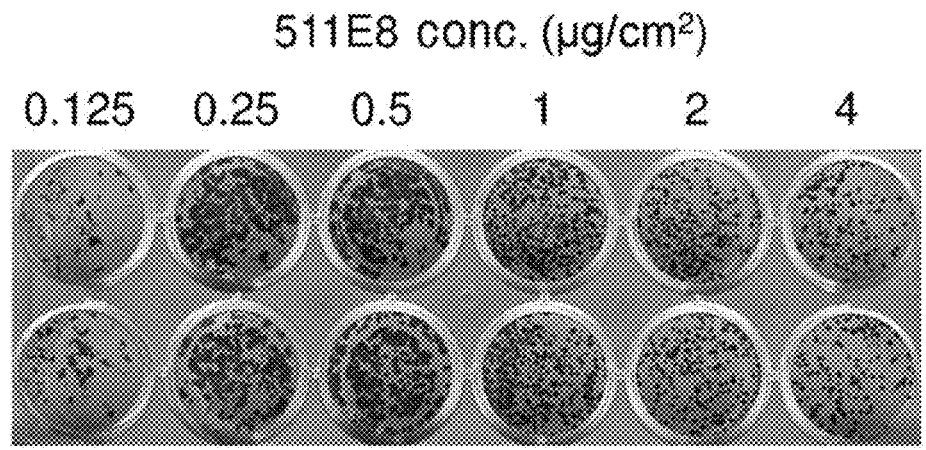
FIG. 1 shows the dependency of human iPS cell growth on the concentration of human laminin 511E8.

The present invention provides a cell culture vessel of which a surface to be in contact with cells is coated with a laminin fragment having integrin α6β1 binding activity or a modified form thereof in a dry state. The cell culture vessel is not particularly limited as long as it is usable for the culture of animal cells. Basically, the cell culture vessel is preferably usable for the culture of mammalian cells, more preferably usable for the culture of mammalian stem cells, still more preferably usable for the culture of human stem cells, and particularly preferably usable for the culture of human pluripotent stem cells. Specific examples of the cell culture vessel include glass or plastic dishes, flasks, multi-well plates, culture slides and microcarriers, and polymer membranes such as a polyvinylidene fluoride membrane.

Laminin is a heterotrimeric molecule consisting of three subunits termed α, β and γ chains. Five kinds of α chains (α1 to α5), three kinds of β chains (β1 to β3) and three kinds of γ chains (γ1 to γ3) are known, and various combinations of these chains result in at least 12 kinds of laminin isoforms. The laminin used in the present invention may be any laminin having integrin α6β1 binding activity, but is particularly preferably at least one kind selected from laminin 511 and laminin 521.

The laminin used in the present invention is preferably a laminin fragment having integrin α6β1 binding activity or a modified form thereof. The laminin fragment may be any laminin fragment consisting of α, β and γ chains of which one or more are fragments shorter than the corresponding full-length chains as long as such a laminin fragment retains integrin α6β1 binding activity. Preferred is a heterotrimeric laminin fragment. The heterotrimer formation of the laminin fragment can be confirmed from, for example, the number of bands detected by SDS-PAGE. The integrin α6β1 binding activity of the laminin fragment can be confirmed by a solid phase binding assay etc.

Among heterotrimeric laminin fragments, laminin E8 is the most preferred in terms of the strength of the integrin binding activity, the efficiency of recombinant expression, and other aspects. The laminin E8 was identified as a fragment having stronger cell-adhesive activity among the fragments obtained by elastase digestion of mouse laminin α1β1γ1 (hereinafter referred to as "mouse laminin 111") (Edgar D., Timpl R., Thoenen H. The heparin-binding domain of laminin is responsible for its effects on neurite outgrowth and neuronal survival. EMBO J., 3: 1463-1468, 1984; and Goodman S L., Deutzmann R., von der Mark K. Two distinct cell-binding domains in laminin can independently promote nonneuronal cell adhesion and spreading. J. Cell Biol., 105: 589-598, 1987). It is presumed that elastase digestion of laminins other than mouse laminin 111 could produce fragments corresponding to the mouse laminin 111 E8, but there is no report on isolation or identification of such E8 fragments. Therefore, the laminin E8 used in the present invention does not have to be an elastase-digested product of laminin, and may be any laminin fragment having a cell-adhesive activity, structure and molecular weight equivalent to those of mouse laminin 111E8.

The laminin fragment having integrin α6β1 binding activity used in the present invention is preferably a heterotrimeric laminin 511 fragment and/or a heterotrimeric laminin 521 fragment, in particular laminin 511E8 and/or laminin 521E8.

The origin of the laminin is not particularly limited and laminins of various organisms can be used. Preferred are laminins of mammals, including but not limited to humans, mice, rats, cattle and pigs. Among these, a human laminin is particularly preferred. In the culture of human stem cells for preparation of materials for human regenerative medicine, a xeno-free (no xenogeneic components are contained in the culture system) environment is required, and for this reason, a human laminin is preferably used.

The laminin may be a native laminin or a mutant laminin that has modification of one or more amino acid residues but retains biological activities of the native laminin. The method for producing the laminin fragment is not particularly limited. For example, the laminin fragment can be obtained by digestion of a full-length laminin with a protease such as elastase, followed by isolation and purification of the fragment of interest. Alternatively, the laminin fragment can be produced as a recombinant protein. In terms of production quantity, quality uniformity, production cost, etc., it is preferred that the laminin fragment is produced as a recombinant protein. The full-length laminin can be produced by purification from highly laminin-expressing cells or produced as a recombinant protein, for example.

The recombinant full-length laminin and the recombinant laminin fragment can be produced by known recombinant techniques, for example, by preparing DNAs encoding full-length or partial-length laminin α, β and γ chains, inserting the DNAs into separate expression vectors, cointroducing the three resulting expression vectors into appropriate host cells, and purifying the expressed trimeric protein by a known method. Examples of the method for producing the recombinant laminin (full-length laminin) include, but are not limited to, the method of Ido et al. (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Combs, James M. Ervasti, and Kiyotoshi Sekiguchi, "Molecular dissection of the α-dystroglycan- and integrin-binding sites within the globular domain of human laminin-10" The Journal of Biological Chemistry, 279, 10946-10954, 2004). Examples of the method for producing the recombinant laminin E8 include, but are not limited to, the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

Information regarding the nucleotide and amino acid sequences of the genes encoding α, β and γ chains which constitute laminins derived from major mammals can be obtained from known databases (e.g., GenBank). The accession numbers of the constituent chains of laminins derived from major mammals including humans are shown in Table 1. Information regarding the nucleotide and amino acid sequences of the constituent chains of laminins derived from other organisms can also be obtained from known databases (e.g., GenBank).

TABLE 1

|  | Amino acid sequence | Nucleotide sequence |
|---|---|---|
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |
| Mouse laminin α5 chain | NP_001074640 | NM_001081171 |
| Mouse laminin β1 chain | NP_032508 | NM_008482 |
| Mouse laminin γ1 chain | NP_034813 | NM_010683 |

TABLE 1-continued

|  | Amino acid sequence | Nucleotide sequence |
|---|---|---|
| Rat laminin α5 chain | NP_001178538 | NM_001191609 |
| Rat laminin β1 chain | NP_001100191 | NM_001106721 |
| Rat laminin γ1 chain | NP_446418 | NM_053966 |

Laminin E8 is a trimeric fragment composed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"), and the molecular weight of the trimer is about 150 to 170 kDa. The α chain E8 generally consists of about 770 amino acids, of which about 230 amino acids from the N-terminus are involved in the trimer formation. The β chain E8 generally consists of about 220 to 230 amino acids. The γ chain E8 generally consists of about 240 to 250 amino acids. The glutamic acid residue at the third position from the C-terminus of the γ chain E8 is essential for the cell-adhesive activity of laminin E8 (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

The modified form of the laminin fragment used in the present invention is, for example, a modified laminin in which a laminin fragment having integrin α6β1 binding activity is conjugated with a cell adhesion molecule or a growth factor binding molecule (see WO 2012/137970). Preferable examples of the cell adhesion molecule include cell adhesion molecules capable of binding to integrins (e.g., fibronectin, collagen, vitronectin, nephronectin, osteopontin, MAEG, tenascin, SVEP1, TGF-β1 latency associated peptide and TGF-β3 latency associated peptide); cell adhesion molecules capable of binding to membrane-bound proteoglycans (e.g., fibronectin, vitronectin, nephronectin and laminin); cell adhesion molecules capable of binding to discoidin domain receptors; cell adhesion molecules capable of binding to dystroglycans (e.g., laminin); and cell adhesion molecules capable of binding to cell surface sugar chains (e.g., concanavalin A, *Dolichos biflorus* agglutinin, *Arachis hypogaea* agglutinin, *Ricinus communis* agglutinin and wheat germ agglutinin).

Preferable examples of the growth factor binding molecule include heparan sulphate proteoglycans such as perlecan, agrin, type XVIII collagen, syndecans 1 to 4 and glypicans 1 to 6; and latent TGF-β binding proteins 1 to 4.

The modified form of the laminin fragment of the present invention can be produced as a recombinant protein by known recombinant techniques. Information regarding the nucleotide and amino acid sequences of the genes encoding known cell adhesion molecules and known growth factor binding molecules can be obtained from known databases (e.g., GenBank).

The cell culture vessel of the present invention is any of the following:

(1) a cell culture vessel of which a surface to be in contact with cells is coated only with a laminin fragment having integrin α6β1 binding activity or a modified form thereof in a dry state;

(2) a cell culture vessel of which a surface to be in contact with cells is coated with a laminin fragment having integrin α6β1 binding activity or a modified form thereof in combination with a laminin fragment having no integrin α6β1 binding activity in a dry state; and
(3) a cell culture vessel of which a surface to be in contact with cells is coated with a laminin fragment having integrin α6β1 binding activity or a modified form thereof in combination with a protein that is neither a laminin nor a laminin fragment, in a dry state.

That is, when a cell culture vessel coated with a laminin fragment having integrin α6β1 binding activity or a modified form thereof (hereinafter referred to as "an α6β1 active fragment or the like") in a dry state is provided in the form of the above (1), (2) or (3), the cell culture vessel can be stored for a long period of time after its production, and even after its long-term storage, can be desirably used for feeder-free human stem cell culture without deterioration in integrin α6β1-dependent cell adhesion or in subsequent cell growth.

In the cell culture vessel of the above (1), the coating concentration of the α6β1 active fragment or the like, which has integrin α6β1 binding activity, is such that the integrin α6β1 binding activity of the α6β1 active fragment or the like exposed to post-coating drying will be preferably 60% or higher, more preferably 70% or higher, further preferably 80% or higher, still further preferably 90% or higher, particularly preferably 95% or higher of that of the same concentration of the same α6β1 active fragment or the like without exposure to post-coating drying. The comparison of integrin α6β1 binding activity can be performed by, for example, the method described in Example 2 later in this specification. The specific procedure is as follows. A solution of an appropriate concentration of the α6β1 active fragment or the like is added to 96-well microtiter plates and the plates are incubated at 4° C. overnight. One of the coated plates is washed with PBS and then dried at room temperature for 1 hour, and another is washed with PBS, but not dried. To these plates, integrin α6β1 is added, the reaction is allowed to proceed for 3 hours, and the amount of the integrin α6β1 bound to each plate is measured.

When the coating concentration of laminin E8 in the cell culture vessel of the above (1) is 0.7 μg/cm$^2$ or higher, the activity of laminin E8, as measured by the method described in Example 2, will be usually 60% or higher of the activity of the same laminin E8 without exposure to post-coating drying. Therefore, the coating concentration of the α6β1 active fragment or the like is 0.7 μg/cm$^2$ or higher, preferably 1.0 μg/cm$^2$ or higher, more preferably 1.2 μg/cm$^2$ or higher, further preferably 1.4 μg/cm$^2$ or higher, and still further preferably 1.5 μg/cm$^2$ or higher. The upper limit is not particularly specified, but the coating concentration is preferably 5.0 μg/cm$^2$ or lower because higher concentrations are not beneficial in terms of production cost and efficacy.

In the cell culture vessel of the above (2), the coating concentration of the α6β1 active fragment or the like is preferably such that the integrin α6β1 binding activity or the human iPS cell growth-supporting activity of the α6β1 active fragment or the like will be reduced when a cell culture vessel is coated with the α6β1 active fragment or the like, dried at room temperature for 1 hour, hermetically sealed and stored at 4° C. for 8 weeks. The degree of reduction in the activity is preferably 70% or less, more preferably 60% or less, still more preferably 50% or less relative to the activity of the α6β1 active fragment or the like without exposure to post-coating drying. The coating concentration of a laminin fragment which is used in combination with the α6β1 active fragment or the like for simultaneous coating and has no integrin α6β1 binding activity (hereinafter, referred to as "another laminin fragment") is such that, by simultaneous coating, the integrin α6β1 binding activity or the human iPS cell growth-supporting activity of the α6β1 active fragment or the like can be maintained at preferably 60% or higher, more preferably 70% or higher, further preferably 80% or higher, still further preferably 90% or higher, particularly preferably 95% or higher relative to that of the same α6β1 active fragment or the like without exposure to post-coating drying.

In the cell culture vessel of the above (2), the coating concentration of the α6β1 active fragment or the like is not particularly limited as long as the coating concentration satisfies the above requirements. The coating concentration of the α6β1 active fragment or the like is preferably 1.5 μg/cm$^2$ or lower, more preferably 1.3 μg/cm$^2$ or lower, further preferably 1.0 μg/cm$^2$ or lower, and still further preferably 0.7 μg/cm$^2$ or lower. Considering the lower limit, the coating concentration is preferably 0.2 μg/cm$^2$ or higher. That is, the coating concentration is preferably 0.2 to 1.5 μg/cm$^2$, more preferably 0.2 to 1.3 μg/cm$^2$, further preferably 0.2 to 1.0 μg/cm$^2$, and still further preferably 0.2 to 0.7 μg/cm$^2$.

As the "another laminin fragment", laminin fragments having no integrin α6β1 binding activity can be used without particular limitation. Heterotrimeric laminin fragments are preferred, and laminin E8 is more preferred. In particular, a laminin 211 fragment is preferred, a heterotrimeric laminin 211 fragment is more preferred, and laminin 211E8 is still more preferred. The "another laminin fragment" may be of only one kind or a combination of two or more kinds. The coating concentration of the "another laminin fragment" is 3 times or more, preferably 4 times or more, more preferably 5 times or more that of the α6β1 active fragment or the like. The upper limit is not particularly specified, and the coating concentration may be, for example, 300 times or less that of the α6β1 active fragment or the like. When the coating concentration of the laminin fragment or a modified form thereof is low, it is preferable that the coating concentration of the "another laminin fragment" is raised in a compensating manner.

In the cell culture vessel of the above (3), the coating concentration of the α6β1 active fragment or the like is preferably such that the integrin α6β1 binding activity or the human iPS cell growth-supporting activity of the α6β1 active fragment or the like will be reduced when a cell culture vessel is coated with the α6β1 active fragment or the like, dried at room temperature for 1 hour, hermetically sealed and stored at 4° C. for 8 weeks. The degree of reduction in the activity is preferably 70% or less, more preferably 60% or less, still more preferably 50% or less relative to the activity of the α6β1 active fragment or the like without exposure to post-coating drying. The coating concentration of a protein which is used in combination with the α6β1 active fragment or the like for simultaneous coating and is neither a laminin nor a laminin fragment (hereinafter, referred to as "another protein") is such that, by simultaneous coating, the integrin α6β1 binding activity or the human iPS cell growth-supporting activity of the α6β1 active fragment or the like can be maintained at preferably 60% or higher, more preferably 70% or higher, further preferably 80% or higher, still further preferably 90% or higher, particularly preferably 95% or higher relative to that of the same α6β1 active fragment or the like without exposure to post-coating drying.

In the cell culture vessel of the above (3), the coating concentration of the α6β1 active fragment or the like is not particularly limited as long as the coating concentration satisfies the above requirements. The coating concentration of the α6β1 active fragment or the like is preferably 1.5 μg/cm$^2$ or lower, more preferably 1.3 μg/cm$^2$ or lower, further preferably 1.0 μg/cm$^2$ or lower, and still further preferably 0.7 μg/cm$^2$ or lower. Considering the lower limit, the coating concentration is preferably 0.2 μg/cm$^2$ or higher. That is, the coating concentration is preferably 0.2 to 1.5 μg/cm$^2$, more preferably 0.2 to 1.3 μg/cm$^2$, further preferably 0.2 to 1.0 μg/cm$^2$, and still further preferably 0.2 to 0.7 μg/cm$^2$.

The "another protein" is not particularly limited, and any protein can prevent drying-caused reduction in the integrin α6β1 binding activity of a laminin fragment having such binding activity. Preferred is a water soluble protein. The molecular weight of the "another protein" is not particularly limited, but is preferably 10000 or more, more preferably 15000 or more, still more preferably 20000 or more, still more preferably 30000 or more, still more preferably 40000 or more, and still more preferably 60000 or more.

Specific examples of the "another protein" include gelatin, human serum albumin, bovine serum albumin, transferrin, myelin basic protein, β-lactoglobulin, glutathione S-transferase, sericin and collagen. Preferred are gelatin, human serum albumin, bovine serum albumin, transferrin, myelin basic protein, β-lactoglobulin, glutathione S-transferase and collagen. More preferred are gelatin, human serum albumin, bovine serum albumin and transferrin. Still more preferred are gelatin and human serum albumin. The "another protein" may be of only one kind or a combination of two or more kinds. The coating concentration of the "another protein" is 20 times or more, preferably 100 times or more, more preferably 500 times or more, still more preferably 1000 or more that of the α6β1 active fragment or the like. The upper limit is not particularly specified, and the coating concentration may be, for example, 5000 times or less that of the β6β1 active fragment or the like.

In the case where gelatin is used as the "another protein", known gelatins for cell culture use can preferably be used. In the case where the cell culture vessel of the present invention is used for cell culture for regenerative medicine, gelatins that have been confirmed safe for medical use are preferably used. Examples of the gelatins that have been confirmed safe for medical use include Nippi high-grade gelatin (Nippi, Inc.) and MEDIGELATIN (Nippi, Inc.).

<Suppressors Capable of Preventing the Activity Reduction>

Both of the "another laminin fragment" and the "another protein" are useful as an active ingredient of a suppressor capable of preventing drying-caused reduction in the integrin α6β1 binding activity of the α6β1 active fragment or the like. Therefore, the present invention can provide a suppressor capable of preventing drying-caused reduction in the integrin α6β1 binding activity of the α6β1 active fragment or the like. The α6β1 active fragment or the like is preferably a laminin 511 or 521 fragment having integrin α6β1 binding activity, and more preferably laminin 511E8 or laminin 521E8. The active ingredient of the suppressor of the present invention is preferably one or more kinds selected from the group consisting of gelatin, human serum albumin, bovine serum albumin, transferrin, myelin basic protein, β-lactoglobulin, glutathione S-transferase, collagen and a laminin α2β1γ1 E8 fragment. When the suppressor of the present invention is used for cell culture using the culture vessel of the present invention, the deterioration in the integrin α6β1 dependent cell adhesion and in subsequent cell growth of the cultured cells can be prevented.

<Method for Producing Cell Culture Vessel>

The cell culture vessel of the present invention can be produced by the following method.

(A) Step of Preparing Coating Solution

The coating solution used is a solution containing a protein to be used as a coating component. The protein contained in the coating solution may be of one kind or a combination of two or more kinds. In the case where a plurality of proteins are used as coating components, it is preferable in terms of working efficiency and convenience to prepare a coating solution containing all the proteins to be used as coating components. The concentration of each protein contained in the coating solution is determined as appropriate in consideration of the coating concentration on the culture vessel's surface to be in contact with cells so that the coating concentration will be a desired value. The solvent usable for the coating solution is not particularly limited unless the solvent reduces the activity of the protein in the coating solution, but preferred is an aqueous solvent. Neutral buffers, which are usually used as solvents for proteins, can preferably be used. Specific examples of the neutral buffers include a physiological saline adjusted to a near-neutral pH with phosphoric acid, citric acid, boric acid, acetic acid, tris(hydroxymethyl)aminomethane, HEPES (4-(2-hydroxyethyl)-1-piperazineethanesulfonic acid) or the like. The coating solution is preferably subjected to sterilization such as filter sterilization before use.

In the case of the production of the cell culture vessel of the above (1), a coating solution containing the laminin fragment having integrin α6β1 binding activity is prepared.

In the case of the production of the cell culture vessel of the above (2), a coating solution containing the laminin fragment having integrin α6β1 binding activity and a coating solution containing the "another laminin fragment" may be separately prepared, or alternatively, a coating solution containing both of them may be prepared. Preferably, a coating solution containing all the proteins to be used as coating components is prepared.

In the case of the production of the cell culture vessel of the above (3), a coating solution containing the laminin fragment having integrin α6β1 binding activity and a coating solution containing the "another protein" may be separately prepared, or alternatively, a coating solution containing both of them may be prepared. Preferably, a coating solution containing all the proteins to be used as coating components is prepared.

(B) Step of Coating Cell Culture Vessel's Surface to be in Contact with Cells with the Desired Protein(s)

The cell culture vessel's surface to be coated is brought into contact with the coating solution(s), and incubation is performed with or without gentle agitation for a certain period of time to allow the protein(s) contained in the coating solution(s) to coat the surface. In the case of coating the bottom surface of a cell culture container, the coating solution is placed into the container. In the case of coating the surface of a sheet- or film-shaped cell culture vessel, the coating solution is applied on top of the area to be coated. In the case of using a plurality of coating solutions, the coating solutions are placed one after another or applied on top of one another to allow the desired protein(s) to coat the surface. As used herein, the "coating with the desired protein(s)" in the case where two or more kinds of proteins are used for the coating does not mean that coating with one of the proteins is performed after the completion of coating with another, but means that coating with the two or more kinds of proteins is performed at the same time. The coating conditions are not particularly limited, but typical coating conditions are about 2 to 18 hours at 4° C. or about 0.5 to 6 hours at room temperature up to 37° C. After the specified time elapses, the coating solution placed or applied is removed. After the removal of the coating solution, the coated surface is preferably washed. The wash solution is not particularly limited, but buffered physiological saline solutions such as PBS are preferably used. This step is preferably performed in a sterile environment, such as a clean room, a clean bench, etc.

(C) Step of Drying the Protein(s) Applied in the Coating Step

The drying method is not particularly limited, and well-known drying methods such as air drying and reduced pressure drying can be used. The drying temperature is not particularly limited unless it causes denaturation or inactivation of the protein(s) applied in the coating step, and drying can preferably be performed at room temperature. The drying temperature is usually about 2 to 40° C., preferably about 4 to 37° C., more preferably about 10 to 30° C., and still more preferably about 15 to 25° C. The drying time is not particularly limited, and drying may be finished once the coated surface is visually confirmed dry without residual liquid. It is preferable to determine in advance an optimal drying time depending on the conditions such as the shape of the cell culture vessel, the composition of the coating solution, the drying method and the drying temperature. This step is preferably performed in a sterile environment, such as a clean room, a clean bench, etc.

The step of drying the protein(s) applied in the coating step may be followed by the step of sterilizing the dried protein(s). Preferable examples of the sterilizing method include radiation sterilization, such as γ-ray sterilization, electron beam sterilization and X-ray sterilization, and ultraviolet radiation sterilization. It is better not to use sterilization methods having the risk of denaturing proteins, such as chemical sterilization including ethylene oxide gas sterilization, and autoclave sterilization using moist heat. In the case where the sterilization step is performed, the production of the cell culture vessel of the present invention is not necessarily performed under strictly sterile conditions and therefore can be achieved at low cost.

The thus-produced cell culture vessel can be stably stored in a hermetically sealed package for a long period of time. The storage temperature is preferably room temperature or lower, and more preferably a further lower temperature (for example, about 4° C.). The present inventors confirmed that the cell culture vessel prepared by drying the protein applied in the coating step, followed by hermetic packaging and storage at 4° C., retained favorable integrin α6β1 binding activity even after an elapse of at least 20 weeks and allowed human iPS cells to favorably grow thereon.

<Method for Culturing Mammalian Cells>

The present invention provides a method for culturing mammalian cells with the use of the above-described cell culture vessel of the present invention. The cell culture vessel of the present invention enables feeder-free culture of cells that are conventionally cultured on feeder cells. In addition, the cell culture vessel of the present invention enables culture of human pluripotent stem cells in a dissociated single-cell state.

The culture method of the present invention is applicable to the culture of any mammalian cells, but is preferably applied to the culture of stem cells. The stem cells refer to cells having a self-renewal capacity and pluripotency, and include somatic stem cells and pluripotent stem cells. Examples of the somatic stem cells include neural stem cells, mesenchymal stem cells and hematopoietic stem cells. Examples of the pluripotent stem cells include ES cells (embryonic stem cells), iPS cells (induced pluripotent stem cells), mGS cells (multipotent germ stem cells) and hybridomas of ES cells and somatic cells. Pluripotent stem cells are more preferred, and ES cells and iPS cells are still more preferred. In addition, the culture method of the present invention can preferably be used for the culture of cells differentiated from the above-mentioned stem cells. The cells differentiated from the stem cells include various cells derived via directed differentiation of the stem cells. That is, the culture method of the present invention can preferably be used for the culture of cells of different stages in the differentiation process of stem cells towards terminally differentiated cells. The mammal as the origin of the cells is not particularly limited, and the examples include humans, mice, rats, cattle and pigs. Particularly preferred are humans. That is, the culture method of the present invention is preferably used for the culture of human stem cells and cells differentiated therefrom. In the case where the culture method of the present invention is used for the culture of human stem cells and cells differentiated therefrom, the modified laminin to be used is preferably of human origin.

The culture medium used for mammalian cell culture in the culture method of the present invention is not particularly limited, and any known recommended culture medium can be used depending on the type of cells. The culture procedure is also not particularly limited, and any known recommended culture procedure is preferably employed depending on the type of cells.

For medical application of human stem cells, the culture method of human stem cells should be standardized so that anyone can culture them on site in clinical practice. To this end, it is necessary to routinize the procedure of such cell culture as much as possible, and it is desirable to commercialize a cell culture vessel coated with the laminin fragment having integrin α6β1 binding activity and make it available to the public. Since the stable long-term storage of a cell culture vessel coated with an optimal concentration of the laminin fragment having integrin α6β1 binding activity (for example, laminin 511E8 or laminin 521E8) is possible according to the present invention, the commercialization of the cell culture vessel coated with the laminin fragment having integrin α6β1 binding activity is possible. Such a precoated culture vessel enables efficient cell culture without variation in coating results among users, thereby being expected to greatly contribute to the dissemination of the medical treatment using human stem cells.

In the course of the development of a technology allowing the laminin fragment to be stably active in a dry state for a long period of time after coating the surface of a cell culture vessel, the present inventors found that, when a cell culture vessel is coated simultaneously with the laminin fragment and a large excess of gelatin, bovine serum albumin, human serum albumin or the like, the drying-caused reduction in the activity of the laminin fragment can be prevented and thereby the activity of the laminin fragment can be maintained at a level comparable to that in the case without post-coating drying. Based on the common technical knowledge in the art, a large excess of gelatin, bovine serum albumin, human serum albumin or the like is supposed to competitively inhibit the adsorption of the laminin fragment to the culture vessel, resulting in remarkably impaired coating with the laminin fragment. In reality, however, a large excess of gelatin or the like hardly compromised the amount and activity of the adsorbed laminin fragment. Although the reason for this result is unclear, the result can be deemed as completely unpredictable from the conventional common technical knowledge.

EXAMPLES

Hereinafter, the present invention will be illustrated in detail by examples, but the present invention is not limited thereto.

<Preparation of Human Recombinant Laminin 511E8>

Human recombinant laminin 511E8 (hereinafter referred to as "511E8") was prepared according to the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins", The Journal of Biological Chemistry, 282, 11144-11154, 2007) as follows.

First, PCR was performed using a cloning plasmid pBluescript KS(+) (Stratagene) as a template to prepare three kinds of pBluescript KS(+) containing a DNA encoding a 6×His tag, a DNA encoding an HA (hemagglutinin) tag or a DNA encoding a FLAG tag inserted at the 5' end of the EcoRV site in the multicloning site. The three sets of primers used for the PCR are as follows.

```
(i) Primers for 6xHis tag insertion
5'-ATGATGATGAAGCTTATCGATACCGT-3'
(forward, SEQ ID NO: 1)

5'-CATCATCATGATATCGAATTCCTGCA-3'
(reverse, SEQ ID NO: 2)

(ii) Primers for HA tag insertion
5'-ATCATATGGATAAAGCTTATCGATACCGT-3'
(forward, SEQ ID NO: 3)

5'-GTGCCAGATTATGCAGATATCGAATTCCT-3'
(reverse, SEQ ID NO: 4)

(iii) Primers for FLAG tag insertion
5'-ATCCTTGTAATCAAGCTTATCGATACCGT-3'
(forward, SEQ ID NO: 5)

5'-GTGCCAGATTATGCAGATATCGAATTCCT-3'
(reverse, SEQ ID NO: 4)
```

Next, PCR was performed using plasmids containing the full-length nucleotide sequences of the α5, β1 and γ1 chains (Ido et al., J. Biol. Chem., 279, 10946-10954, 2004) as templates to amplify the region corresponding to α5 (Ala$^{2534}$-Ala$^{3327}$), the region corresponding to β1 (Leu$^{1561}$-Leu$^{1786}$) and the region corresponding to γ1 (Asn$^{1362}$-Pro$^{1608}$), respectively. The primers used for the PCR are as follows.

```
(iv) Primers for amplification of α5 chain E8
fragment
5'-GCTGCCGAGGATGCTGCTGGCCAGG-3'
(forward, SEQ ID NO: 6)

5'-CTAGGCAGGATGCCGGGCGGGCTGA-3'
(reverse, SEQ ID NO: 7)

(v) Primers for amplification of β1 chain E8
fragment
5'-CTTCAGCATAGTGCTGCTGACATTG-3'
(forward, SEQ ID NO: 8)

5'-TTACAAGCATGTGCTATACACAGCAAC-3'
(reverse, SEQ ID NO: 9)

(vi) Primers for amplification of γ1 chain E8
fragment
5'-AATGACATTCTCAACAACCTGAAAG-3'
(forward, SEQ ID NO: 10)

5'-CTAGGGCTTTTCAATGGACGGGGTG-3'
(reverse, SEQ ID NO: 11)
```

The amplified cDNAs were separately inserted into the EcoRV site in the multicloning site of the above-prepared three kinds of pBluescript KS (+) containing a tag-encoding sequence. From each resulting plasmid, the region containing the inserted DNA fragment and the 5'-terminal tag-encoding sequence was amplified. Then, the amplified product was digested with restriction enzymes EcoRI and HindIII. The digested fragment was inserted into the corresponding restriction site of pSecTag2B, a mammalian cell expression vector (Invitrogen), to give an expression vector for the human α5 chain E8 fragment (containing the 6×His tag in the N-terminal region), an expression vector for the human β1 chain E8 fragment (containing the HA tag in the N-terminal region), and an expression vector for the human γ1 chain E8 fragment (containing the FLAG tag in the N-terminal region).

For expression of 511E8, the three expression vectors were introduced into human embryonic kidney 293F cells (purchased from Invitrogen). Into 300 mL of 293F cells (1.0×10$^6$ cells/mL), 180 μg each of the three expression vectors were co-transfected with transfection reagents 293fectin (trade name, Invitrogen) and Opti-MEM (trade name, Invitrogen), the cells were cultured for 72 hours, and then the culture medium was harvested. The harvested culture medium was centrifuged at 1,000×g for 10 minutes, and the supernatant was further centrifuged at 15,000×g for 30 minutes for removal of remaining cells and insoluble matter. To the supernatant, 5 mL of Ni-NTA agarose (QIAGEN) was added and the protein of interest was allowed to bind thereto by overnight incubation. The Ni-NTA agarose was collected and washed successively with TBS(−) (tris-buffered saline without Ca or Mg) and 10 mM imidazole/TBS(−), and elution was performed with 200 mM imidazole/TBS(−). The eluted fractions were subjected to SDS-PAGE followed by silver staining. To the 511E8-containing fraction, 2 mL of ANTI-FLAG M2 Affinity Gel (Sigma) was added and the mixture was rotated at 4° C. overnight. The affinity gel was transferred into an Econo Column, which was then washed with TBS(−) containing 1 mM PMSF. Subsequently, elution was performed with TBS(−) containing 100 μg/mL FLAG peptide (Sigma). After the eluted fractions were subjected to silver staining, the 511E8-containing fractions were combined and dialyzed against TBS (−).

<Preparation of Human Recombinant Laminin 521E8>

Human recombinant laminin 521E8 (hereinafter referred to as "521E8") was prepared by a method similar to that described above for human recombinant laminin 511E8. The specific procedure is as follows. An expression vector for the human α5 chain E8 fragment (containing the 6×His tag in the N-terminal region), an expression vector for the human β2 chain E8 fragment (containing the HA tag in the N-terminal region), and an expression vector for the human γ1 chain E8 fragment (containing the FLAG tag in the N-terminal region) were prepared and then were transfected into human embryonic kidney 293F cells. The cells were cultured for 72 hours and the culture medium was then harvested. Subsequently, purification by affinity chromatography using nickel-NTA agarose and ANTI-FLAG M2 Affinity Gel was performed as was the case with the laminin 511E8. The expression vector for the human β2 chain E8 fragment was prepared according to the method of Taniguchi et al. (Yukimasa Taniguchi, Hiroyuki Ido, Noriko Sanzen, Maria Hayashi, Ryoko Sato-Nishiguti, Sugiko Futaki, and Kiyotoshi Sekiguchi, "The C-terminal region of laminin β chains modulates the integrin binding affinities of laminins" The Journal of Biological Chemistry, 7820-7831, 2009).

<Preparation of Laminin 511E8 Conjugated with Heparan Sulphate Chain-Attached Domain of Perlecan>

A modified form of laminin in which the domains I to III of human perlecan (hereinafter referred to as "Pln-D1/2/3", which contains heparan sulphate chain attachment sites) were fused to the N-terminal region of the human recombinant laminin 511E8 (hereinafter referred to as "Plus#3 laminin E8") and a modified form of laminin in which the domain I of human perlecan (hereinafter referred to as "Pln-D1") was fused to the C-terminal region of the human recombinant laminin 511E8 (hereinafter referred to as "Plus#5 laminin E8") were prepared.

For the preparation of the Plus#3 laminin E8, an expression vector for a Pln-D1/2/3 fused human laminin β1 chain E8 fragment was prepared by joining a DNA fragment encoding a mouse Ig-kappa chain V-J2-C signal peptide, a DNA fragment encoding Pln-D1/2/3, a DNA fragment encoding HA tag, and a DNA fragment encoding the β1 chain E8 in this order from the 5' end as described in WO 2012/137970. The expression vector for the Pln-D1/2/3 fused human laminin β1 chain E8 fragment, an expression vector for the human α5 chain E8 fragment (containing the 6×His tag in the N-terminal region), and an expression vector for the human γ1 chain E8 fragment (containing the FLAG tag in the N-terminal region) were mixed and then were transfected into human embryonic kidney 293F cells. The cells were cultured for 72 hours and the culture medium was then harvested. The Plus#3 laminin E8 secreted in the culture medium was purified by affinity chromatography using nickel-NTA agarose and ANTI-FLAG M2 Affinity Gel as was the case with the laminin 511E8.

For the preparation of the Plus#5 laminin 58, an expression vector for a Pln-D1 fused human laminin α5 chain E8 fragment was prepared as follows. First, a DNA fragment encoding the C-terminal region (Leu$^{611}$-Pro$^{813}$) of the human laminin α5 chain E8 fragment fused with the linker sequence between the domains G3 and G4 of the human laminin al chain (DAEDSKLLPEPRAFP, SEQ ID NO: 12) was amplified by PCR using the expression vector for the human laminin α5 chain E8 fragment as a template and the following primers.

```
(i) Primers for amplification of the linker
sequence-fused fragment
5'-CCTCAAGCGGCTGAACACGACAGGCG-3'
(forward, SEQ ID NO: 13)

5'-ATATGGATCCTGGAAAAGCCCGGGGCTCTGGCAAGAGCTTGCTGTCC
TCTGCATCAGGCCCCAGGCCCGG-3'
(reverse, SEQ ID NO: 14; this primer contains the
BamHI restriction enzyme recognition sequence)
```

The DNA fragment thus obtained was digested with restriction enzymes AscI (the recognition sequence for this restriction enzyme is present in the DNA sequence encoding the C-terminal region of the human laminin α5 chain E8 fragment) and BamHI. The resulting fragment was named DNA fragment 1.

Next, PCR was performed using an expression vector for human perlecan (Shaoliang Li, Chisei Shimono, Naoko Norioka, Itsuko Nakano, Tetsuo Okubo, Yoshiko Yagi, Maria Hayashi, Yuya Sato, Hitomi Fujisaki, Shunji Hattori, Nobuo Sugiura, Koji Kimata and Kiyotoshi Sekiguchi, "Activin A Binds to Perlecan through Its Pro-region That Has Heparin/Heparan Sulfate Binding Activity", Journal of Biological Chemistry, 285 (47), 36645-36655, 2010) as a template to amplify a DNA fragment encoding a sequence of the region corresponding to PlnD1 (Gly$^{25}$-Pro$^{196}$) with a C-terminal His tag. The primers used for the PCR are as follows.

```
(ii) Primers for amplification of PlnD1 sequence
5'-ATATATATGGATCCGGCCTGAGGCCATACGATGGCTTGTCTCTG-3'
(forward, SEQ ID NO: 15; this primer contains the
BamHI restriction enzyme recognition sequence)

5'-ATATATATGCGGCCGCCTAATGATGATGATGATGATGTGGGAACTC
CGCCACTGTGCCCAG-3'
(reverse, SEQ ID NO: 16; this primer contains the
NotI restriction enzyme recognition sequence)
```

The obtained DNA fragment was digested with restriction enzymes BamHI and NotI, and the resulting fragment was named DNA fragment 2.

The expression vector for the human laminin α5 chain E8 fragment was digested with restriction enzymes AscI and NotI, and the digested fragment encoding the N-terminal region of the human laminin α5 chain E8 fragment (Met$^1$-Asp$^{610}$) was joined with the above DNA fragments 1 and 2, to give an expression vector for the Pln-D1 fused human laminin α5 chain E8 fragment.

The expression vector for the Pln-D1 fused human laminin α5 chain E8 fragment, an expression vector for the human β1 chain E8 fragment (containing the HA tag in the N-terminal region), and an expression vector for the human γ1 chain E8 fragment (containing the FLAG tag in the N-terminal region) were mixed and then were transfected into human embryonic kidney 2935 cells. The cells were cultured for 72 hours and the culture medium was then harvested. Subsequently, purification by affinity chromatography using nickel-NTA agarose and ANTI-FLAG M2 Affinity Gel was performed as was the case with the laminin 511E8.

<Preparation of Human Recombinant Laminin 211E8>

Human recombinant laminin 211E8 (hereinafter referred to as "211E8") was prepared by a method similar to that described above for human recombinant laminin 511E8. The specific procedure is as follows. An expression vector for the human α2 chain E8 fragment (containing the 6×His tag in the N-terminal region), an expression vector for the human β1 chain E8 fragment (containing the HA tag in the N-terminal region), and an expression vector for the human γ1 chain E8 fragment (containing the FLAG tag in the N-terminal region) were prepared and then were transfected into human embryonic kidney 293F cells. Subsequently, purification by affinity chromatography using nickel-NTA agarose and ANTI-FLAG M2 Affinity Gel was performed as was the case with the laminin 511E8. The expression vector for the human α2 chain E8 fragment was prepared according to the method of Taniguchi et al. (Yukimasa Taniguchi, Hiroyuki Ido, Noriko Sanzen, Maria Hayashi, RyokoSato-Nishiguti, Sugiko Futaki, and Kiyotoshi Sekiguchi, "The C-terminal region of laminin β chains modulates the integrin binding affinities of laminins" The Journal of Biological Chemistry, 7820-7831, 2009).

<Culture Method of Human iPS Cell Line 201B7>

A human iPS cell line, 201B7, was obtained from RIKEN BioResource Center (#HPS0063). According to the recommended culture method, 201B7 cells were maintained on SNL76/7 feeder cells (ECACC #07032801), which had been mitotically inactivated by mitomycin-C treatment, with a culture medium for primate ES cells (ReproCELL Inc. #RCHEMD001) supplemented with 4 ng/mL of human basic fibroblast growth factor (bFGF, Sigma #F0291). Before use in evaluation tests, the 201B7 cells maintained as described above were seeded in a dissociated single-cell state on 6-well culture plates (Becton Dickinson #353046) coated with the 511E8 and cultured without feeder cells for 6 to 8 days.

The specific procedure is as follows. The colonies of the 201B7 cells maintained on the feeder cells were treated with a solution of 0.25% trypsin (Life Technologies #15090-046)/0.1 mg/mL type IV collagenase (Life Technologies #17104-019)/20% KnockOut Serum Replacement (Life Technologies #10828-028)/1 μM $CaCl_2$ to remove the feeder cells, and then treated with 0.5× TrypLE Select (Life Technologies #12563-011) at 37° C. for 4 minutes. The cells were washed with PBS (pH 7.4) (Life Technologies #10010-023) and a 1:1 mixed medium of TeSR2 (STEMCELL Technologies #05860) and NutriStem (Biological Industries #05-100-1) supplemented with Y27632 (Merck Millipore #688000) at a final concentration of 10 μM was added. The cells were collected with a cell scraper and dissociated into single cells by pipetting. After cell counting, the cells were seeded at a density of $1.3 \times 10^4$ cells/well or $2.6 \times 10^4$ cells/well on a 6-well culture plate coated with 0.5 μg/cm² 511 E8 and cultured in a TeSR2/NutriStem (1:1) mixed medium supplemented with Y27632 under a humidified atmosphere of 5% $CO_2$/95% air at 37° C. At 1, 3 and 5 days post-seeding, the culture medium was replaced with a TeSR2/NutriStem (1:1) mixed medium (without Y27632), and from then on, the medium replacement was performed daily. Expansion culture was continued until 6 to 8 days post-seeding, when the cells covered about 80% of the usable surface area of the culture vessel, and the cells were subjected to the experiments shown below (hereinafter, the cells at this point are referred to as 511E8P1, which means the cells at the first passage on the 511E8-coated vessel after maintained on feeder cells).

<Culture Method of Human iPS Cell Line Tic>

A human iPS cell line, Tic, was obtained from the Japanese Collection of Research Bioresources (JCRB) Cell Bank (#JCRB1331). According to the recommended culture method, Tic cells were maintained on primary mouse embryonic fibroblast (MEF, Merck Millipore #PMEF-H) feeder cells with a maintenance culture medium for Tic cells supplemented with 10 ng/mL human bFGF. The maintenance culture medium for Tic cells was a KnockOut DMEM/F-12 culture medium (Life Technologies #12660-012) containing 20% KnockOut Serum Replacement/nonessential amino acids (Life Technologies #11140-050)/2 mM L-glutamine (Life Technologies #25030-081)/0.1 mM 2-mercaptoethanol (Life Technologies #21985-023). Before use in evaluation tests, the Tic cells maintained as described above were seeded in a dissociated single-cell state on 6-well culture plates coated with Matrigel and cultured without feeder cells for 6 to 8 days.

The specific procedure is as follows. The Tic cells maintained on the feeder cells were treated with dispase II (Roche Applied Science #4942078) at 37° C. for 7 minutes, and then treated with TrypLE Express (Life Technologies #12605-010) at 37° C. for 4 minutes. After addition of a mTeSR1 medium (STEMCELL Technologies #05850) supplemented with Y27632 at a final concentration of 10 the cells were collected with a cell scraper and dissociated into single cells by pipetting. After cell counting, the cells were seeded at a density of $1.3 \times 10^4$ cells/well or $2.6 \times 10^4$ cells/well on a 6-well culture plate coated with 3 μg/cm² of Matrigel for human ES cells (Becton Dickinson #354277) and cultured in a mTeSR1 culture medium supplemented with Y27632 under a humidified atmosphere of 5% $CO_2$/95% air at 37° C. At 1, 3 and 5 days post-seeding, the culture medium was replaced with a mTeSR1 medium (without Y27632), and from then on, the medium replacement was performed daily. Expansion culture was continued until 6 to 8 days post-seeding, when the cells covered about 80% of the usable surface area of the culture vessel, and the cells were subjected to the experiments shown below (hereinafter, the cells at this point are referred to as MGP1, which means the cells at the first passage on the Matrigel-coated vessel after maintained on feeder cells).

Example 1: Confirmation of 511E8 Concentration Dependency of Human iPS Cell Growth 511E8 was diluted to 0.5 to 16 μg/mL in PBS (pH 7.4) (Life Technologies #10010-023) and the diluted solutions were added at 500 μL/well to a 24-well cell culture plate (Becton Dickinson #353047, usable surface area: 2 cm²/well) so that the final concentrations would be 0.125 to 4 μg/cm². The plate was incubated with gentle agitation at 4° C. overnight (about 18 hours) to give a 511E8-coated plate. After coating, the plate was washed with PBS (pH 7.4), a TeSR2/NutriStem (1:1) mixed medium was added, and the plate was kept in a $CO_2$ incubator at 37° C. until use. The 201B7 cells at 511E8P1 were washed with PBS (pH 7.4), treated with 0.5×TrypLE Select at 37° C. for 4 minutes, and dissociated into single cells in a TeSR2/NutriStem (1:1) mixed medium supplemented with 10 μM Y27632. After cell counting, the cells were seeded at a density of $1.3 \times 10^3$ cells/cm² on the 511E8-coated 24-well culture plate and cultured under a humidified atmosphere of 5% $CO_2$/95% air at 37° C. At 1, 3, 5 and 6 days post-seeding, the culture medium was replaced with a TeSR2/NutriStem (1:1) mixed medium (without Y27632), and at 7 days post-seeding, the growth and state of the cells were evaluated by alkaline phosphatase staining. The alkaline phosphatase staining was performed using a Leukocyte Alkaline Phosphatase Kit (Sigma-Aldrich #86R-1KT) according to the attached recommended protocol.

The results are shown in FIG. 1. From the results shown in FIG. 1, it is evident that the 201B7 cells did not sufficiently grow in the wells coated with a low concentration (0.125 μg/cm²) of 511E8. It is also evident that, in the wells coated with high concentrations (2 to 4 μg/cm²), the 201B7 cells formed colonies but not sufficiently large ones. That is, it was shown that the 511E8 coating concentration appropriate for the growth of the 201B7 cells was 0.25 to 1 μg/cm². The alkaline phosphatase activity is one of the undifferentiation markers and remains at a high level in an undifferentiated state. All the cell colonies which had grown under the indicated conditions were positive for the alkaline phosphatase staining and therefore thought to be maintained in an undifferentiated state.

Example 2: Reduction of the Activity of 511E8 by Post-Coating Drying

In order to examine whether it is possible to store a cell culture vessel subjected to coating with 511E8 at an optimal concentration (0.5 μg/cm²) and subsequent drying, a 511E8-coated plate was dried for 1 hour and the influence of the drying was examined in terms of integrin binding activity and human iPS cell adhesion and growth.

The α6β1 integrin binding activity of the 511E8 applied to coat the plate was measured according to the method described in Ido et al. (J. Biol. Chem., 282, 11144-11154, 2007). The specific procedure is as follows. A 511E8 solution diluted to 2 μg/mL in PBS (pH 7.4) was added at 80 μL/well to a 96-well microtiter plate (Becton Dickinson #353072, usable surface area: 0.32 cm$^2$/well) so that the final concentration would be 0.5 μg/cm$^2$. The plate was incubated with gentle agitation at 4° C. overnight (about 18 hours) to give a 511E8-coated plate. The plate was washed with PBS (pH 7.4) and air-dried at room temperature for 1 hour. In the same manner as above except that the drying step was not performed, a 511E8-coated plate was prepared and used as a control. The plates were treated with 10 nM α6β1 integrin in the presence of 1 mM MnCl$_2$ for 3 hours, and the amount of the α6β1 integrin bound to each plate was measured as the absorbance of a chromogenic substrate at 490 nm.

Figure 2:
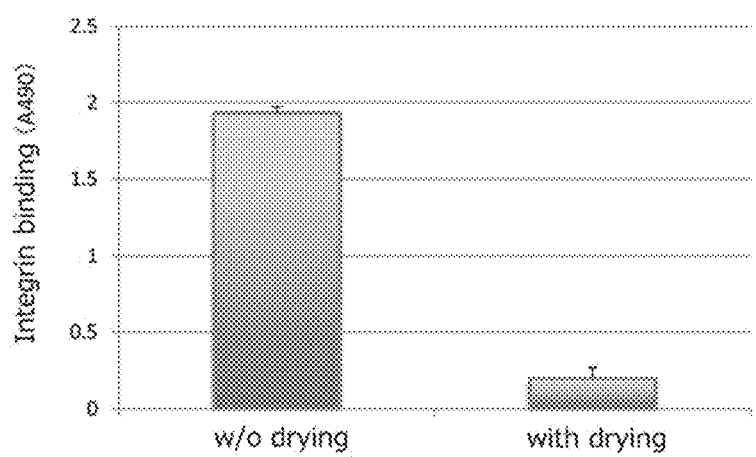
FIG. 2 shows the results of the examination of the α6β1 integrin binding activity of a plate which had been coated with human laminin 511E8 and then exposed to post-coating drying.

The results are shown in FIG. 2. As is clear from FIG. 2, in the plate which had been coated with 0.5 μg/cm$^2$ 511 E8 and exposed to drying conditions for 1 hour, the α6β1 integrin binding activity of the 511E8 was remarkably reduced.

According to the previous report, the adhesion of human embryonic stem cells (ES cells) onto 511E8 is inhibited by concurrent treatment with function blocking antibodies against α6 integrin and β1 integrin (Miyazaki et al. Nature Communications and 3: 1236. doi: 10.1038/ncomms2231, 2012). As shown above, the α6β1 integrin binding activity of the 511E8 applied to coat the plate was reduced by drying, which would be expected to influence the adhesion and growth of human iPS cells. This possibility was examined in an experiment in which human iPS cells were cultured on a 511E8-coated plate exposed to post-coating drying. In the same manner as described in Example 1, a 24-well culture plate was coated with 511E8 at a concentration of 0.5 μg/cm$^2$, washed with PBS (pH 7.4), and air-dried at room temperature for 1 hour. In the same manner as above except that the drying step was not performed, a 511E8-coated plate was prepared and used as a control. In the same manner as described in Example 1, the 201B7 cells at 511E8P1 and the Tic cells at MGP1 were dissociated into single cells and seeded at a density of 1.3×10$^3$ cells/cm$^2$, and at 7 days post-seeding, the morphology of the cells was observed after alkaline phosphatase staining.

Figure 3:
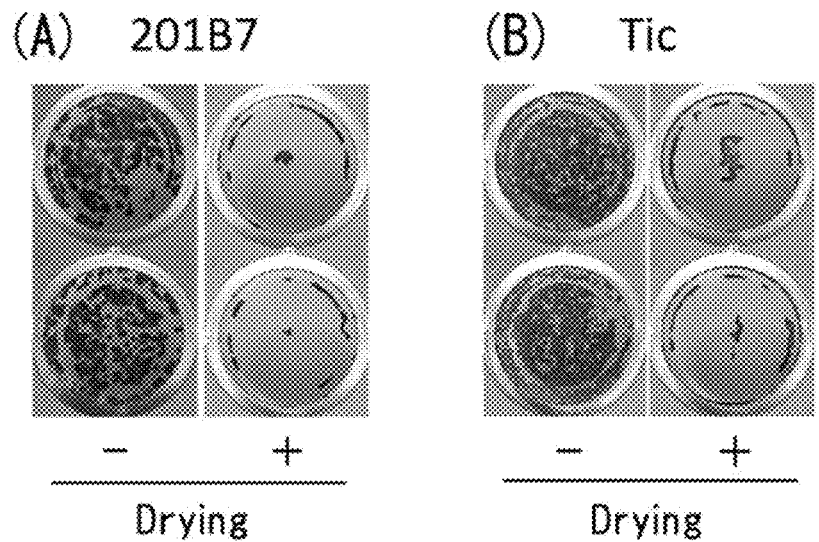
FIG. 3 shows the results of the examination of the influence of post-coating drying on the adhesion and growth of human iPS cells in an experiment using a plate which had been coated with human laminin 511E8 and then exposed to post-coating drying. (A) shows the results with 201B7 cells and (B) shows the results with Tic cells.

The results are shown in FIG. 3. (A) shows the results with 201B7 cells and (B) shows the results with Tic cells. Both the cell lines grew on the 511E8-coated plate without exposure to post-coating drying, but did not sufficiently grow on the 511E8-coated plate exposed to 1-hour drying. This was possibly because of the drying-caused reduction in the α6β1 integrin binding activity as shown in FIG. 2.

Example 3: Concentration Dependency of the Reduction in Integrin Binding Activity by Post-Coating Drying The coating concentrations at which the drying-caused reduction in the integrin binding activity of 511E8 as shown in FIG. 2 would occur were explored. In the same manner as described in Example 2, 511E8 solutions diluted to 0.25 to 16 μg/mL in PBS (pH 7.4) were added at 80 μL/well to a 96-well microtiter plate so that the final concentrations would be 0.063 to 2 μg/cm$^2$, and the plate was incubated at 4° C. overnight to give a 511E8-coated plate. The plate was washed with PBS (pH 7.4) and air-dried at room temperature for 1 hour. In the same manner as above except that the drying step was not performed, a 511E8-coated plate was prepared and used as a control. In the same manner as described in Example 2, the plates were treated with 10 nM α6β1 integrin and the amount of the bound integrin was measured.

Figure 4:
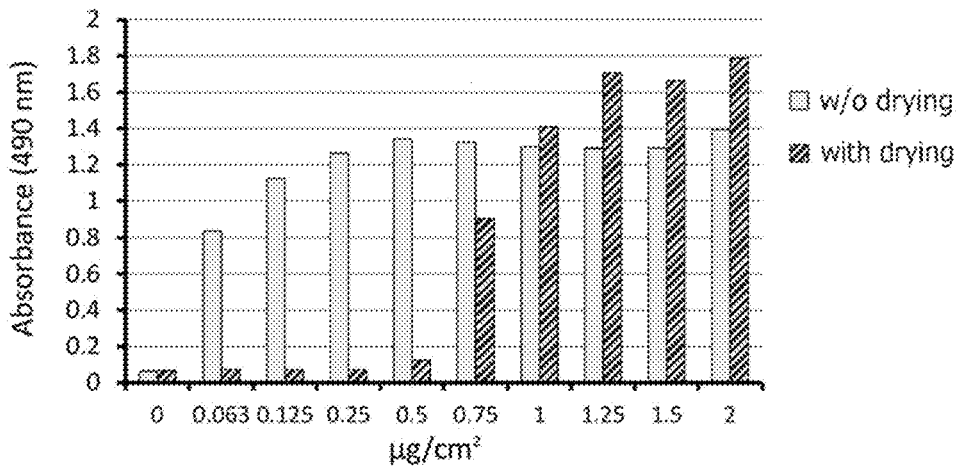
FIG. 4 shows the results of the examination of the concentration dependency of the drying-caused reduction in the integrin binding activity of human laminin 511E8.

The results are shown in FIG. 4. The amount of the bound integrin increased along with an increase in the coating concentration of 511E8 up to 0.5 μg/cm$^2$ and reached the plateau at higher coating concentrations under the conditions where the plate had not been subjected to post-coating drying. On the other hand, when the plate had been dried after coating, the amount of the bound integrin was remarkably lower at coating concentrations of 0.5 μg/cm$^2$ or lower as was the case with the results shown in FIG. 2, but the amount of the bound integrin was lower by only about 30% at a coating concentration of 0.75 μg/cm$^2$, and comparable or even higher at coating concentrations of 1 μg/cm$^2$ or higher. That is, the susceptibility of 511E8 to post-coating drying was dependent on the coating concentration.

Example 4: Screening of Suppressor Candidates for Preventing the Activity Reduction Various substances were used in combination with 511E8 for simultaneous coating and tested for their potential to prevent the activity reduction of 511E8 exposed to post-coating drying.

The suppressor candidates used were 10% glycerol (Wako Pure Chemical Industries #075-00616), 20% sucrose (Sigma #28-0010), 20% glucose (Wako Pure Chemical Industries #049-31165), 20% sorbitol (Sigma #S-3889-500G), 20% trehalose (Hayashibara #TH223), 0.5% Tween20 (Sigma #P5927), 10% polyethylene glycol with an average molecular weight of 4000 (PEG4000, Sigma #24-3680), 10% polyethylene glycol 6000 (PEG6000, Nacalai Tesque #28254), 10% polyethylene glycol 8000 (PEG8000, MP Biomedicals #25322-68-3), 1% arginine (Nacalai Tesque #03321), 1% glycine (Sigma #12-1210-5), 1% lysine (Nacalai Tesque #20806), 1% proline (Nacalai Tesque #29001), 0.1% bovine serum albumin (BSA, Sigma #A7906-100G), and 0.05% gelatin from porcine skin (Sigma #G1890-100G). Each substance was mixed with 2 μg/mL (final concentration: 0.5 μg/cm$^2$) of 511E8 in PBS (pH 7.4), and the resulting mixture was added at 80 μL/well to a 96-well microtiter plate (usable surface area: 0.32 cm$^2$/well). The plate was incubated at 4° C. overnight, and the coated plate was dried and used for the evaluation of the activity of 511E8 exposed to drying.

Specifically, after coating with a mixture of 511E8 and each candidate, the plate was washed with PBS (pH 7.4), dried at room temperature for 24 hours, wrapped with a strip of Parafilm, sealed in a hermetic packaging material (DRY KEEP aluminum pouch, SASAKI CHEMICAL #T-PE-30-231AL), and stored at 4° C. for 1 week. The plate was treated with 10 nM α6β1 integrin, and the α6β1 integrin binding activity (the amount of the α6β1 integrin bound to the plate) was measured. On the day before the measurement, another 96-well microtiter plate was coated at 0.5 μg/cm$^2$ with 511E8 diluted in PBS (pH 7.4) at 4° C. overnight without subsequent drying. After incubation with 10 nM α6β1 integrin, the amount of the bound integrin (absorbance at 490 nm) was measured and used as an activity level of 100%, based on which the integrin binding activities of the 511E8 exposed, to post-coating drying in the presence of the above-listed candidate substances were compared.

Figure 5:
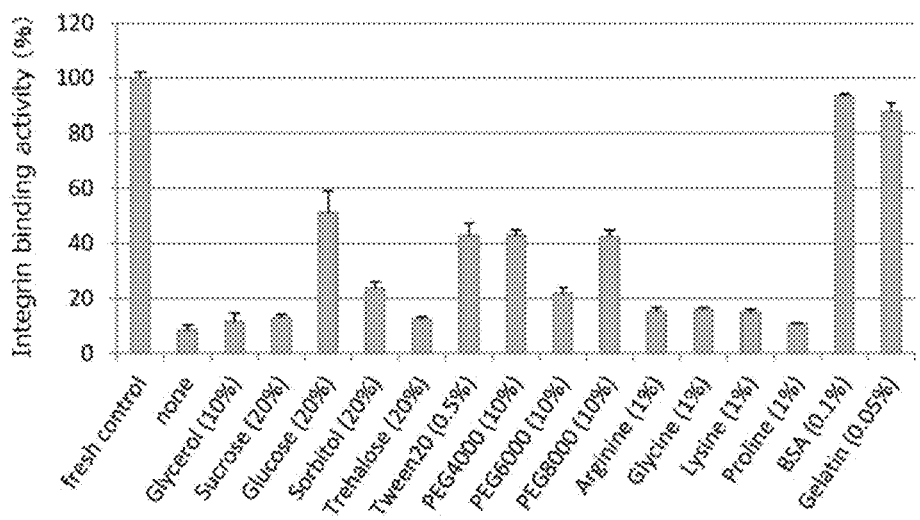
FIG. 5 shows the results of the efficacy evaluation of various suppressor candidates for preventing the activity reduction.

The results are shown in FIG. 5. In the plate which had been coated with only 511E8, dried and stored ("none" in the figure), the binding activity was reduced to 10% or lower of that in the control, i.e., the plate which had been coated with only 511E8 without subsequent drying. In the comparison of the candidate substances, in the presence of glucose or some others, the reduction in the integrin binding activity was prevented and the activity remained at about 40%. Furthermore, in the presence of BSA or gelatin, the integrin binding activity was maintained at about 90% in each case. The results of a Kruskal-Wallis test and a Dunn's multiple comparison test showed that there were significant differences at a significance level of 1% in the cases of BSA and gelatin. These results suggest a possibility that BSA and gelatin, and their related proteins have potent effect as a suppressor protein capable of preventing the activity reduction.

Example 5: Preventive Effects of Proteins Other than BSA and Gelatin on Activity Reduction BSA and gelatin, the substances shown in Example 4 to have a strong preventive effect on the activity reduction, are proteins. Accordingly, other proteins were also tested for their preventive effect on the reduction in the activity of 511E8 under drying conditions in order to examine whether any and all proteins have preventive effect on the drying-caused activity reduction, or only specific proteins have such effect.

In addition to BSA and gelatin, which were used in Example 4, human serum albumin (Bio-Pure HSA, Biological Industries #05-720-1D), sericin (Pure Sericin, Wako Pure Chemical Industries #167-22681), glutathione S-transferase (GST, Thermo Fisher Scientific #20237), transferrin (Becton Dickinson #354204), myelin basic protein (MBP, Merck Millipore #13-104), and β-lactoglobulin A (Sigma #L7880) were used in the test. Each substance was mixed with 2 μg/mL 511E8 (final concentration: 0.5 μg/cm$^2$) so that the final concentration would be 500 μg/mL. In the same manner as described in Example 4, the resulting mixture was added at 80 μL/well to a 96-well microtiter plate (usable surface area: 0.32 cm$^2$/well), and the plate was incubated at 4° C. overnight to give a coated plate. The coated plate was washed with PBS (pH 7.4), dried at room temperature for 1 hour, and treated with 10 nM α6β1 integrin, and the amount of the bound integrin was measured. In the same manner as described in Example 4, another 96-well microtiter plate was coated with 511E8 at a final concentration of 0.5 μg/cm$^2$ without subsequent drying, followed by incubation with 10 nM α6β1 integrin. The amount of the bound integrin (absorbance at 490 nm) was measured and used as an activity level of 100%, based on which the integrin binding activities of the 511E8 exposed to post-coating drying in the presence of the above-listed proteins were compared.

Figure 6:
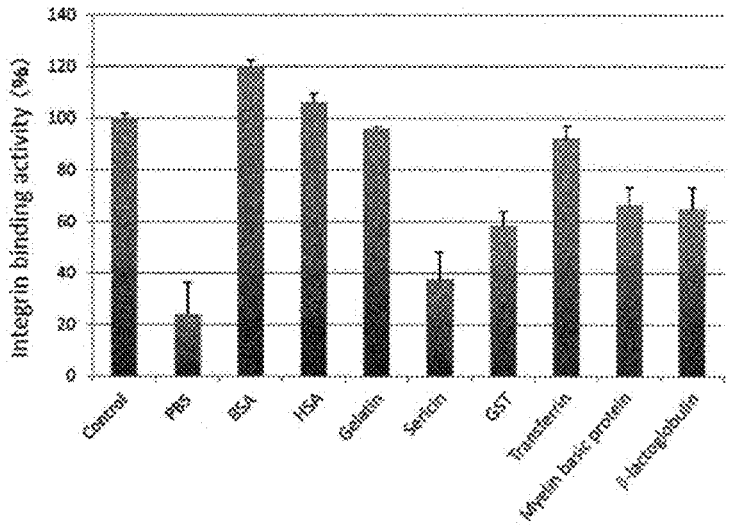
FIG. 6 shows the results of the examination of the effects of various proteins to prevent the activity reduction.

The results are shown in FIG. 6. In the presence of any of the tested proteins, the integrin binding activity was maintained at a higher level than that in the conditions where no proteins were added (PBS only). In particular, human serum albumin and transferrin were shown to have more potent preventive effect on the activity reduction than those other than BSA and gelatin. That is, the preventive effect on the activity reduction of the 511E8 exposed to drying is not unique to some specific proteins, but is common to proteins in general, albeit to different extents.

Example 6: Concentration Dependency of Preventive Effect of Protein Component on Activity Reduction In Examples 4 and 5, the 96-well microtiter plate was coated with 0.5 μg/cm$^2$ 511 E8, that is, the plate was coated with a 511E8 solution diluted to 2 μg/mL. Thus, the amounts of BSA and gelatin used as the suppressor proteins capable of preventing the activity reduction were 500 and 250 times the amount of the 511E8 protein used, respectively. With such a background, it was examined whether the integrin binding activity of the adsorbed 511E8 would be influenced by the amount of the suppressor protein used. The specific procedure is as follows. 511E8 and gelatin were separately diluted with PBS (pH 7.4), and the diluted solutions were mixed so that the final concentration of the 511E8 would be 0.25, 0.5 or 1.0 μg/cm$^2$ and so that the final concentration of gelatin would be 1.7 to 500 μg/mL. In the same manner as described in Example 4, a 96-well microtiter plate was coated with the resulting mixtures. The coated plate was washed with PBS (pH 7.4) without subsequent drying, treated with 10 nM α6β1 integrin, and the amount of the bound integrin was measured.

Figure 7:
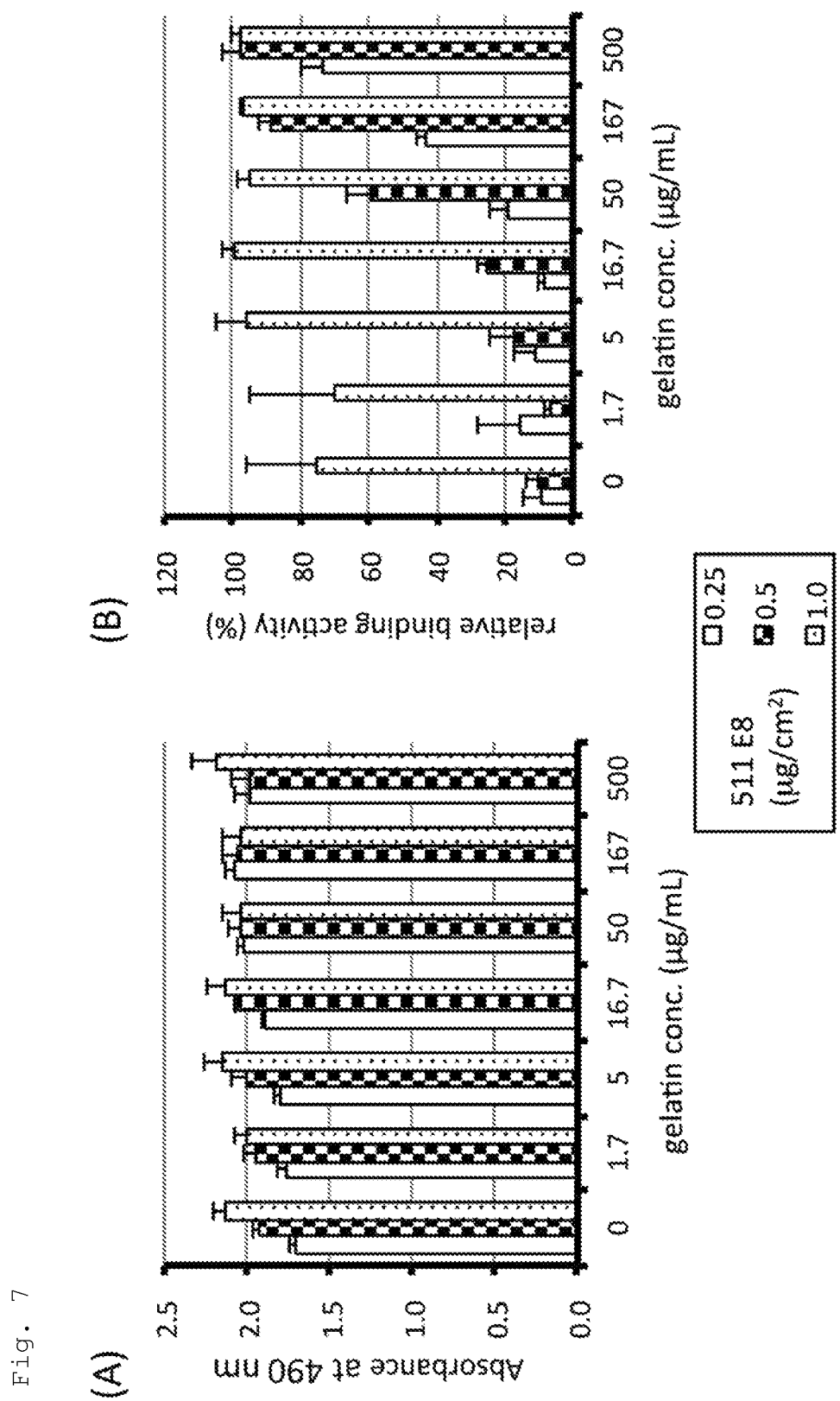
FIG. 7 shows the results of the examination of the concentration dependency of the preventive effect on the activity reduction in an experiment using three-graded concentrations of human laminin 511E8 in combination with seven-graded concentrations of gelatin. (A) shows the results of the α6β1 integrin binding activity as measured without post-coating drying, and (B) shows the results of the α6β1 integrin binding activity as measured with post-coating drying.

The results are shown in FIG. 7 (A). The decline in the integrin binding activity with an increase in gelatin concentration was not observed irrespective of the concentration of 511E8 examined. At a 511E8 concentration of 0.25 μg/cm$^2$, the integrin binding activity was maintained even in the presence of up to 500 times excess of gelatin. Rather, the integrin binding activity was increased to a level comparable to those attained at higher concentrations of 511E8 by the addition of gelatin. It is a well-known fact that gelatin does not have binding activity for α6β1 integrin, and the α6β1 integrin binding activity was not detected at all in the case of coating with 500 μg/mL gelatin alone, although data are not shown in the figure.

Next, the concentration dependency of the preventive effect on the drying-caused activity reduction was examined. A plate was coated with the same combinations of 511E8 and gelatin as shown in FIG. 7 (A), dried for 1 hour, and treated with 10 nM integrin α6β1, and the amount of the bound integrin was measured.

The results are shown in FIG. 7 (B). In the case of coating with 511E8 alone at 1.0 μg/cm$^2$, inactivation by drying was less clearly observed, as shown in Example 3, and at this concentration, no difference in the integrin binding activity was produced by the addition of gelatin. In the case where the 511E8 concentration was 0.5 μg/cm$^2$, gelatin showed preventive effect on the activity reduction in a concentration dependent manner. That is, the integrin binding activity of 511E8 was reduced at the gelatin concentrations of 16.7 μg/mL or lower, but the binding activity was maintained at a level comparable to that in the case without post-coating drying at the gelatin concentrations of 167 μg/mL or higher. In addition, in the presence of 50 μg/mL gelatin, a weak preventive effect was observed. In the case where the 511E8 concentration was 0.25 μg/cm$^2$, the integrin binding activity was reduced to about 70% even in the presence of 500 μg/mL gelatin, and reduced to about 40% in the presence of 167 μg/mL gelatin. This preventive effect of gelatin on the activity reduction was also dependent on its concentration, but the overall strength of such effect was lower than that at the 511E8 concentration of 0.5 μg/cm$^2$. That is, a protein component showed preventive effect on the activity reduction of 511E8 in a concentration dependent manner, and the concentration of 511E8 also influenced the strength of such effect.

Example 7: Examination of Timing of Addition of Suppressor Protein Capable of Preventing the Activity Reduction In order to determine the optimal timing for the addition of a suppressor protein capable of preventing the activity reduction, the preventive effect on the drying-caused activity reduction was examined in an experiment in which the addition of the suppressor protein was simultaneous with, before or after coating with 511E8. 511E8 was added at a final concentration of 0.5 µg/cm$^2$ to 96-well microtiter plates, and the plates were incubated at 4° C. overnight to give coated plates. Gelatin was added as the suppressor protein at a final concentration of 300 µg/mL on the following three conditions.
(1) The suppressor protein diluted in PBS (pH 7.4) was added to a plate, followed by incubation at room temperature for 3 hours for precoating, and 511E8 was added thereto.
(2) The suppressor protein and 511E8 were mixed in advance and the mixture was added to a plate for simultaneous coating.
(3) After coating a plate with 511E8 overnight, the suppressor protein was added to the plate, and the plate was incubated at room temperature for 3 hours for postcoating.

The 511E8-coated plates thus obtained were washed with PBS (pH 7.4), dried at room temperature for 24 hours, and treated with 10 nM α6β1 integrin, and the amount of the bound integrin was measured. Another 96-well microtiter plate was coated with 511E8 at a final concentration of 0.5 µg/cm$^2$ without subsequent drying, and then treated with 10 nM α6β1 integrin. The amount of the bound integrin (absorbance at 490 nm) was measured and used as an activity level of 100%, based on which the integrin binding activities of the 511E8 exposed to post-coating drying in the above conditions were compared.

Figure 8:
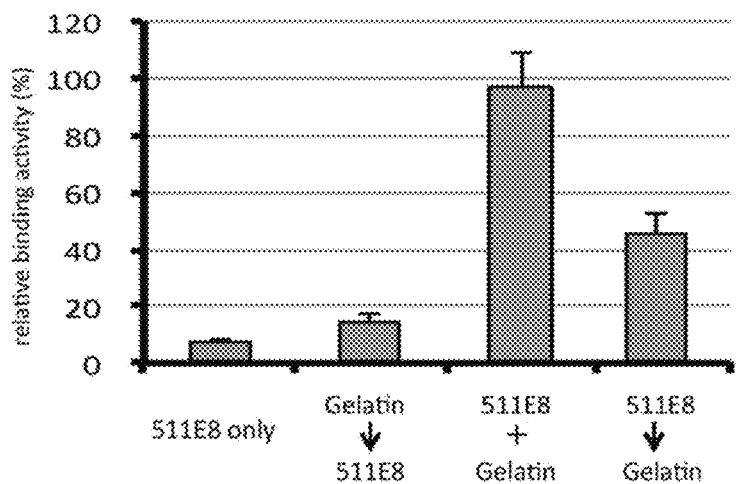
FIG. 8 shows the results of the examination of the timing of addition of the indicated suppressor protein capable of preventing the activity reduction.

The results are shown in FIG. 8. In the figure, condition (1) is represented as Gelatin→511E8, condition (2) is represented as Gelatin+511E8, and condition (3) is represented as 511E8→Gelatin. As is clear from FIG. 8, the highest preventive effect on the activity reduction was found with the case of simultaneous addition of gelatin and 511E8 (condition (2)) among the three conditions. The integrin binding activity in condition (2) was maintained almost at the control level even after exposure to severe drying conditions, i.e. after 24-hour drying. Although data are not shown in the figure, it was confirmed that the α6β1 integrin binding activity measured in the case of condition (1) without post-coating drying was comparable to that in the case of coating with 511E8 alone. The above results showed that simultaneous coating was the most effective way to prevent the activity reduction.

Example 8: Persistency of the Effect of Suppressor Protein Capable of Preventing the Activity Reduction It was shown above that 511E8 maintained its integrin binding activity after post-coating drying in the presence of the suppressor protein. Next, it was examined whether the integrin binding activity of 511E8 could be sustained in a dry state for a long period of time. A 24-well cell culture plate was coated at a final concentration of 0.5, 1.0 or 2.0 µg/cm$^2$ with 511E8 diluted in PBS (pH 7.4) in the presence or absence of 300 µg/mL gelatin. The coated plate was dried at room temperature for 1 hour, sealed similarly as described in Example 4, and stored at 4° C. After a given time of storage, the 201B7 cells were dissociated into single cells and seeded at a density of 2.6×10$^3$ cells/cm$^2$ onto the plate, as described in Example 1. At 7 days post-seeding, the morphology of the cells was observed after alkaline phosphatase staining.

Figure 9:
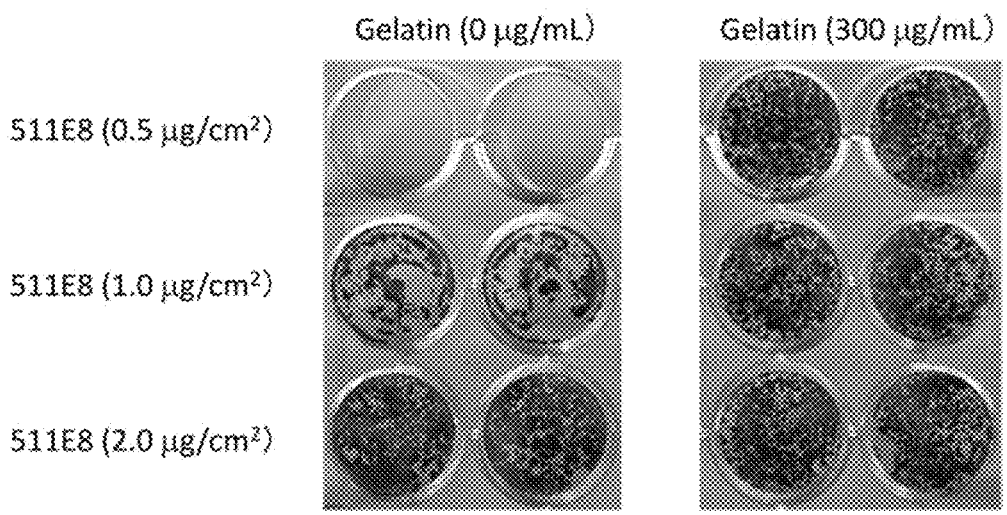
FIG. 9 shows the images of the human iPS cells cultured for 7 days on a plate which had been stored for 8 weeks after post-coating drying to examine the persistency of the effect of the indicated suppressor protein capable of preventing the activity reduction.

The results with the plate stored for 8 weeks are shown in FIG. 9. As is clear from FIG. 9, in the absence of the suppressor protein, the human iPS cells hardly proliferated in the wells coated with 0.5 µg/cm$^2$ 511 E8, and cell growth in the wells coated with 1.0 µg/cm$^2$ 511 E8 was still insufficient and inferior to that in the wells coated with 2.0 µg/cm$^2$ 511 E8. On the other hand, cell growth was sufficient at any of the indicted 511E8 concentrations in the wells coated with 511E8 in the presence of the suppressor protein. The above results suggest that a plate coated with 511E8 in combination with the suppressor protein can be stored in a dry state for a long period of time.

Example 9: Concentration Dependent Preventive Effect of BSA on Activity Reduction In the same manner as described in Example 6, 511E8 was diluted with PBS (pH 7.4) so that the final concentration would be 0.5 µg/cm$^2$, and the diluted 511E8 solution was mixed with BSA at various concentrations up to 3000 µg/mL. A 96-well microtiter plate was coated with the resulting mixtures at 4° C. overnight, washed with PBS (pH 7.4), and dried at room temperature overnight. After 1 week of storage at 4° C., the plate was treated with 10 nM α6β1 integrin and the amount of the bound integrin was measured to evaluate the concentration dependent preventive effect of BSA on the reduction in the activity of 511E8. On the day before the measurement, another 96-well microtiter plate was coated at 0.5 µg/cm$^2$ with 511E8 diluted in PBS (pH 7.4) at 4° C. overnight without subsequent drying. After incubation with 10 nM α6β1 integrin, the amount of the bound integrin (absorbance at 490 nm) was measured and used as an activity level of 100%, based on which the integrin binding activities of 511E8 in the presence of BSA at various concentrations were compared.

Figure 10:
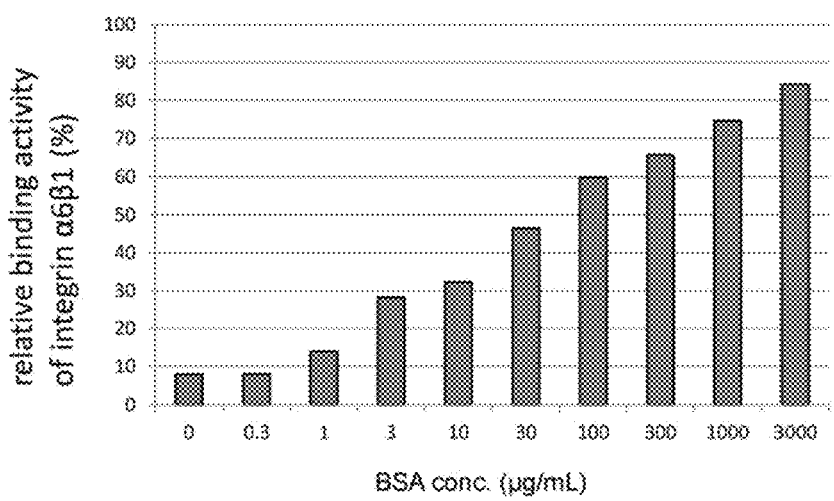
FIG. 10 shows the results of the examination of the concentration dependent effect of BSA to prevent the activity reduction.

The results are shown in FIG. 10. As is clear from FIG. 10, the preventive effect of BSA on the activity reduction as shown in FIGS. 5 and 6 was dependent on its concentration as was the case with gelatin, and the BSA concentrations of 100 µg/mL or higher were effective to maintain the integrin binding activity at a high level. These results suggest that, for the proteins shown to prevent the activity reduction, their effect is dependent on their concentration in general.

Example 10: Examination of Preventive Effect on the Reduction in Activities of 511E8 and Full-Length Laminin 511

In order to examine whether the suppressor proteins capable of preventing the activity reduction of 511E8 would be also effective for other proteins to be used for coating as a culture matrix, the efficacy of the suppressor proteins to prevent the activity reduction of a full-length laminin 511 was examined in comparison with 511E8. The full-length laminin 511 used was prepared according to the method described in Ido et al. (J. Biol. Chem., 279, 10946-10954, 2004). The experimental procedure was the same as described in Example 4. The specific procedure is as follows. 511E8 was diluted with PBS (pH 7.4) so that the final concentration would be 0.5 or 1.0 μg/cm², and the full-length laminin was diluted with PBS (pH 7.4) so that the final concentration would be 16.0 or 32.0 μg/cm². Each diluted solution was mixed with BSA or gelatin (final concentration: 300 μg/mL each), and a plate was coated with the resulting mixtures at 4° C. overnight. The coated plate was washed with PBS (pH 7.4), dried at room temperature for 24 hours, and treated with 10 nM α6β1 integrin, and the amount of the bound integrin was measured.

Figure 11:
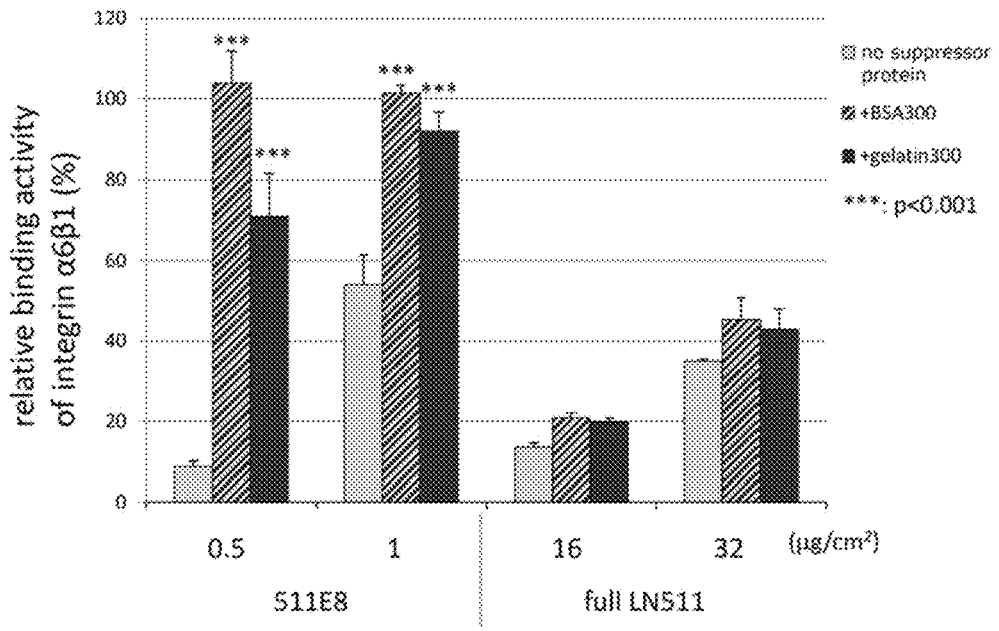
FIG. 11 shows the results of the examination of the preventive effect on the reduction in the activities of human laminin 511E8 and a full-length human laminin 511.

The results are shown in FIG. 11. The vertical axis represents the relative activity determined from the measurement of the amount of the bound α6β1 integrin (absorbance at 490 nm) upon incubation with 10 nM α6β1 integrin. The level of 100% corresponds to the amount of the α6β1 integrin bound to the plate that had been coated with 511E8 or the full-length laminin 511 alone at the indicated concentrations without subsequent drying. In the absence of either of the suppressor proteins, the integrin binding activities of both 511E8 and the full-length 511 were remarkably reduced by 24-hour drying. The efficacy of the suppressor proteins to prevent the drying-caused activity reduction was analyzed by a two-way analysis of variance and the Bonferroni's method. In the case of coating with 511E8 in the presence of BSA or gelatin, the activity reduction was significantly prevented at a significance level of 0.1% at any indicated condition. However, in the case of coating with the full-length laminin 511, no significant effect was observed at any indicated condition (at a significance level of 5%). These results suggest that the suppressor proteins effective for preventing the activity reduction of 511E8, such as BSA and gelatin, are not always effective for proteins other than 511E8 to be used for coating as a culture matrix, and that their efficacy may greatly vary with the molecular nature such as the shape and amino acid sequence of the protein to be used for coating as a culture matrix. That is, it is suggested that the suppressor protein effective for preventing the activity reduction of 511E8 is effective for other proteins having similar molecular nature such as similar shape as that of 511E8.

Example 11: Preventive Effect on the Reduction in Activity of 521E8

In order to examine whether the suppressor proteins would exert a similar preventive effect on the activity reduction of a laminin E8 other than 511E8, the efficacy of the suppressor proteins to prevent the activity reduction of 521E8 was examined in comparison with 511E8. 521E8 is an E8 fragment derived from laminin 521 and is composed of an α5 chain E8 fragment and a γ1 chain E8 fragment, which are also the components of 511E8, and a β2 chain E8 fragment, which is different from the β chain component of 511E8. In the same manner as described in Example 4, 511E8 and 521E8 were separately diluted with PBS (pH 7.4) so that the final concentrations would be 0.5 and 1.0 μg/cm², each diluted solution was mixed with BSA, gelatin or human serum albumin (HSA) (final concentration: 500 μg/mL each), and a plate was coated with the resulting mixtures at 4° C. overnight. The coated plate was washed with PBS (pH 7.4), dried at room temperature for 1 hour, and treated with 10 nM α6β1 integrin, and the amount of the bound integrin was measured.

Figure 12:
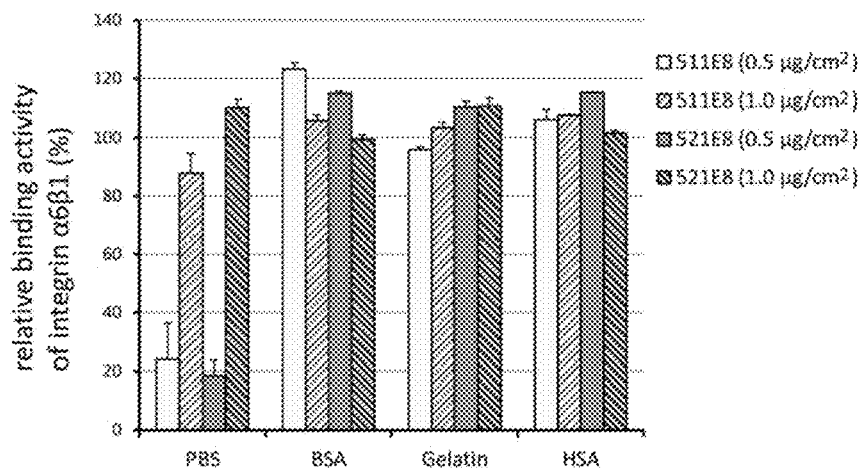
FIG. 12 shows the results of the examination of the preventive effect on the reduction in the activity of human laminin 521E8.

The results are shown in FIG. 12. The vertical axis represents the relative activity determined from the measurement of the amount of the bound α6β1 integrin (absorbance at 490 nm) upon incubation with 10 nM α6β1 integrin. The level of 100% corresponds to the amount of the α6β1 integrin bound to the plate that had been coated with 511E8 alone at the indicated concentrations without subsequent drying. Taniguchi et al. (J. Biol. Chem., 284, 7820-7831, 2009) previously reported that the binding affinities of 511E8 and 521E8 for α6β1 integrin are comparable. In this example, in the case where the post-coating drying had not been performed, the absorbances measured at 490 nm as an indicator of the amount of the bound α6β1 integrin were 2.62±0.05 (average±standard deviation) for 0.5 μg/cm² 511 E8 and 2.75±0.02 for 0.5 μg/cm² 521 E8; and were 2.96±0.03 for 1.0 μg/cm² 511 E8 and 2.83±0.11 for 1.0 μg/cm² 521 E8, showing that the amounts of the α6β1 integrin bound to 511E8 and 521E8 were comparable.

In the case where the post-coating drying had been performed for 1 hour, the integrin binding activity of 521E8 decreased in a pattern similar to that of 511E8, as is clear from FIG. 12. That is, in the case of coating at 1.0 μg/cm², inactivation by drying was hardly observed, but in the case of coating at 0.5 μg/cm², remarkable reduction in the integrin binding activity was observed. The reduction in the binding activity by drying was almost completely prevented by the addition of BSA, gelatin or HSA, as was the case with 511E8. That is, these suppressor proteins were shown to be effective for preventing the activity reduction of not only 511E8, but also an E8 fragment of another laminin isoform.

Example 12: Preventive Effect of 211E8 on the Activity Reduction of 511E8

It was examined whether a laminin E8 other than 511E8 also has preventive effect on the drying-caused activity reduction. The E8 fragment used was a laminin 211E8 fragment (hereinafter, referred to as 211E8), which is a laminin fragment having no binding activity for α6β1 integrin. The specific procedure is as follows. 511E8 diluted with PBS (pH 7.4) (final concentration: 0.4 μg/cm²) was mixed with 211E8 diluted with PBS (pH 7.4) (final concentration: 0, 0.8 or 1.6 μg/cm²), and a 96-well microtiter plate was coated with the resulting mixtures at 4° C. overnight. The coated plate was washed with PBS (pH 7.4), dried at room temperature for 24 hours, and treated with 10 nM α6β1 integrin, and the amount of the bound integrin was measured. The present inventors previously confirmed that 211E8 has no binding activity for α6β1 integrin (Taniguchi et al. J. Biol. Chem., 284, 7820-7831, 2009).

Figure 13:
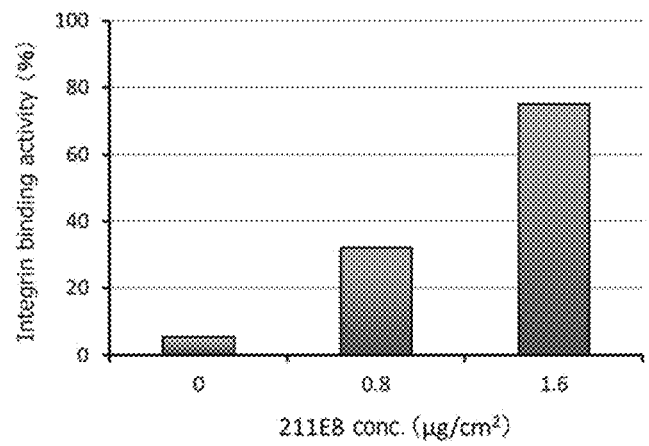
FIG. 13 shows the results of the examination of the preventive effect of human laminin 211E8 on the reduction in the activity of human laminin 511E8.

The results are shown in FIG. 13. The α6β1 integrin binding activity is expressed as a relative value on the assumption that the amount of the bound integrin in the case of coating with 0.4 μg/cm² 511 E8 without subsequent drying (the absorbance at 490 nm was 1.07) was a level of 1000. As is clear from FIG. 13, the integrin binding activity was restored to about 30% in the presence of 0.8 μg/cm² 211 E8, and to about 80% in the presence of 1.6 μg/cm² 211 E8. These results showed that a laminin E8 fragment other than 511E8 can be used as a suppressor protein capable of preventing the activity reduction of 511E8. In addition, such a laminin E8 fragment other than 511E8 was shown to be effective as the suppressor protein in quite a smaller amount to prevent the drying-caused activity reduction as compared with other proteins such as BSA and gelatin.

Example 13: Preventive Effect on the Activity Reduction of Modified Laminin Fragments (1)

In order to examine whether the suppressor proteins could also prevent the drying-caused activity reduction of a modified laminin fragment, the efficacy of the suppressor proteins to prevent the activity reduction was examined for two modified forms of 511E8 (Plus#3 laminin E8 and Plus#5 laminin E8) in which 511E8 is conjugated with the heparan sulphate chain-attached domain of perlecan, and compared with the efficacy for 511E8. The Plus#3 laminin E8 is a modified form of 511E8 in which the domains I to III of perlecan are conjugated to the N-terminal region of the β1 chain E8 fragment, and the Plus#5 laminin E8 is a modified form of 511E8 in which the domain I of perlecan is conjugated to the C-terminal region of the α5 chain E8 fragment. In the same manner as described in Example 4, the Plus#3 laminin E8 and the Plus#5 laminin E8 were separately diluted with PBS (pH 7.4) so that the final concentrations would be 0.56 µg/cm², each diluted solution was mixed with human serum albumin (HSA; final concentration: 500 µg/mL) or gelatin (final concentration: 300 µg/mL or 2000 µg/mL), and a 96-well microtiter plate was coated with the resulting mixtures at 37° C. for 1 hour. After removal of the coating solution, the coated plate was dried at room temperature for 22 hours, and treated with 10 nM α6β1 integrin, followed by the measurement of the amount of the bound integrin. The amount of the α6β1 integrin bound to the plate coated with the Plus#3 laminin 58 or the Plus#5 laminin E8 alone without subsequent drying was used as a control.

Figure 14:
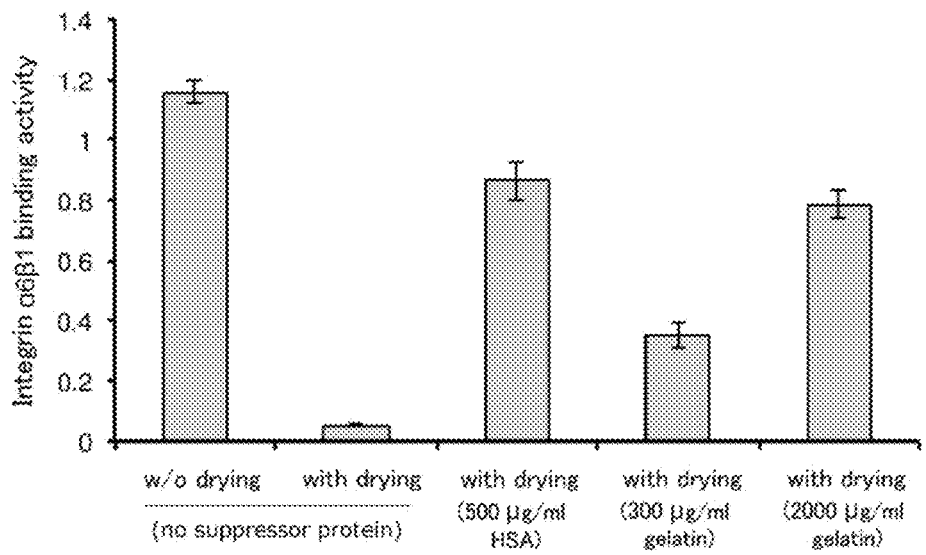
FIG. 14 shows the results of the examination of the preventive effect on the reduction in the activity of a modified human laminin 511E8 (Plus#3 laminin E8) in which the heparan sulphate chain-attached domain of perlecan is conjugated to the N-terminal region of the β1 chain E8 fragment.
Figure 15:
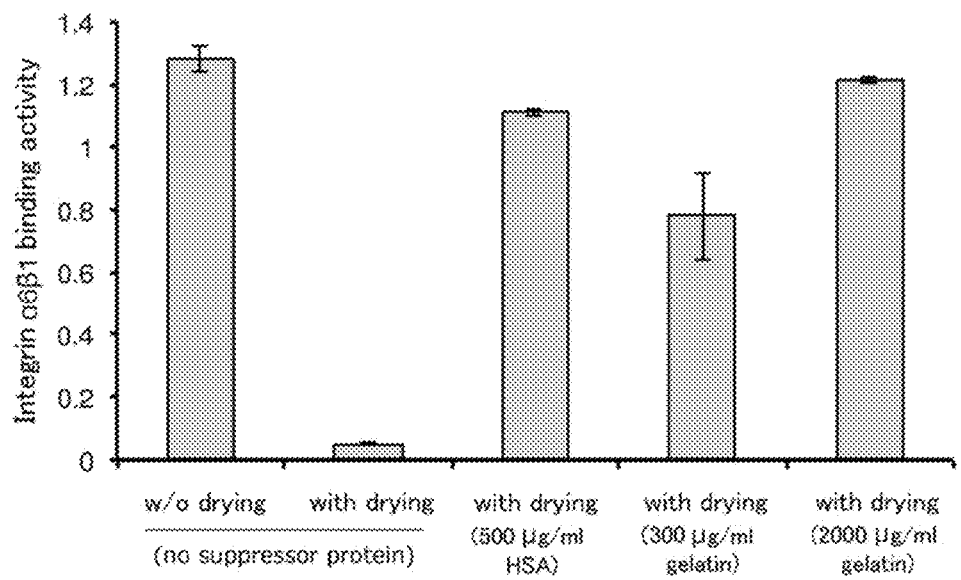
FIG. 15 shows the results of the examination of the preventive effect on the reduction in the activity of a modified human laminin 511E8 (Plus#5 laminin E8) in which the heparan sulphate chain-attached domain of perlecan is conjugated to the C-terminal region of the α5 chain E8 fragment.

The results with the Plus#3 laminin E8 are shown in FIG. 14 and the results with the Plus#5 laminin E8 are shown in FIG. 15. The vertical axis represents the amount of the bound α6β1 integrin (absorbance at 490 nm). In the case of coating with the Plus#3 laminin E8 or the Plus#5 laminin E8 alone followed by drying, the integrin binding activity was remarkably reduced, as is clear from FIGS. 14 and 15. On the other hand, in the case of coating with the Plus#3 laminin E8 or the Plus#5 laminin E8 in the presence of human serum albumin or gelatin followed by drying, the reduction in the integrin binding activity was prevented. In particular, as for the Plus#5 laminin E8 exposed to drying in the presence of human serum albumin or gelatin, the integrin binding activity was maintained at a level of about 90% as shown in FIG. 15. These results showed that the suppressor proteins of the present invention are effective for preventing the activity reduction of not only a laminin fragment, but also a modified form thereof.

Example 14: Preventive Effect on the Activity Reduction of Modified Laminin Fragment (2)

The efficacy of the suppressor proteins capable of preventing the activity reduction of a modified laminin fragment was further examined. A 24-well cell culture plate (Becton Dickinson #353047) was coated with the Plus#5 laminin E8 (final concentration: 0.56 µg/cm') alone or with the Plus#5 laminin E8 (final concentration: 0.56 µg/cm²) in the presence of human serum albumin (HSA; final concentration: 500 µg/mL) or gelatin (final concentration: 300 µg/mL or 2000 µg/mL) and dried at room temperature for 22 hours. Human iPS cells (201B7 cells) were seeded on the coated plate at a density of $7\times10^3$ cells/cm² and cultured under a humidified atmosphere of 5% $CO_2$/95% air at 37° C. for 1 week. The culture medium used was a TeSR2/NutriStem (1:1) mixed medium. Similarly, 201B7 cells were seeded and cultured for 1 week on another 24-well cell culture plate which had been coated with the Plus#5 laminin E8 (final concentration: 0.56 µg/cm²) without subsequent drying. The growth of the human iPS cells after one-week culture was evaluated by alkaline phosphatase staining.

Figure 16:
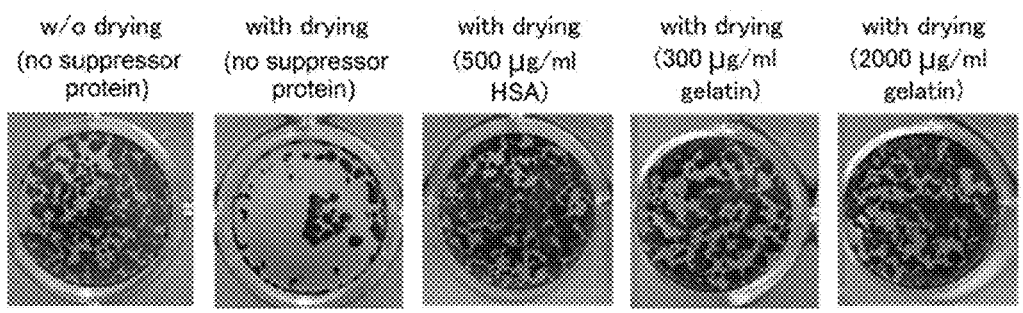
FIG. 16 shows the images of the human iPS cells cultured for 1 week on a plate which had been coated with a modified human laminin 511E8 (Plus#5 laminin E8) in which the heparan sulphate chain-attached domain of perlecan is conjugated to the C-terminal region of the α5 chain E8 fragment in the absence or presence of the indicated suppressor proteins capable of preventing the activity reduction, and subsequently dried.

The results are shown in FIG. 16. As is clear from FIG. 16, the growth of the human iPS cells seeded on the Plus#5 laminin E8-coated plate was comparable to that observable on a 511E8-coated plate, demonstrating that the Plus#5 laminin E8 is effective as a culture matrix for human iPS cells. The resulting colonies of human iPS cells were uniformly positive for the alkaline phosphatase staining and therefore thought to be maintained in an undifferentiated state. On the other hand, on the plate which had been coated with the Plus#5 laminin E8 in the absence of any of the suppressor proteins and subsequently dried, cell growth was remarkably reduced. However, in the case of coating with the Plus#5 laminin E8 in the presence of human serum albumin or gelatin at a final concentration of 300 µg/mL or higher followed by drying, the growth of human iPS cells was not reduced and was comparable to or higher than that in the case of coating with the Plus#5 laminin E8 without subsequent drying. In addition, the human iPS cells were positive for the alkaline phosphatase staining and therefore thought to be maintained in an undifferentiated state. The above results showed that the suppressor proteins of the present invention are effective for preventing the activity reduction of not only a laminin fragment, but also a modified form thereof.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A cell culture vessel characterized in that a surface to be in contact with cells is coated with a laminin fragment in a dry state having integrin α6β1 binding activity or a modified form thereof in a dry state in combination with a protein that is neither a laminin nor a laminin fragment in a dry state,
the laminin fragment having integrin α6β1 binding activity being derived from at least one kind selected from laminin α5β1γ1 E8 fragment and laminin α5β2γ1 E8 fragment,
the modified form thereof being the laminin α5β1γ1 E8 fragment or the laminin α5β2γ1 E8 fragment conjugated with a cell adhesion molecule or a growth factor binding molecule,
wherein the laminin fragment having integrin α6β1 binding activity or the modified form thereof is coated on the surface at a coating concentration of 0.2 to 1.0 μg/cm², and the protein that is neither a laminin nor a laminin fragment has a coating concentration 100 times or more that of the laminin fragment having integrin α6β1 binding activity or the modified form thereof,
wherein the protein that is neither a laminin nor a laminin fragment has a molecular weight of 10000 or higher.

2. The cell culture vessel according to claim 1, wherein the protein that is neither a laminin nor a laminin fragment is one or more kinds selected from the group consisting of gelatin, human serum albumin, bovine serum albumin, transferrin, myelin basic protein, β-lactoglobulin, glutathione S-transferase and collagen.

3. The cell culture vessel according to claim 1, wherein the cell culture vessel is produced through the steps of coating the surface to be in contact with cells with the laminin fragment having integrin α6β1 binding activity or the modified form thereof, and the protein that is neither a laminin nor a laminin fragment, and subsequently drying the laminin fragment having integrin α6β1 binding activity or the modified form thereof, and the protein that is neither a laminin nor a laminin fragment.

4. A method for producing the cell culture vessel according to claim 1,
the method comprising the steps of:
(A) preparing a coating solution containing the laminin fragment having integrin α6β1 binding activity or the modified form thereof, and the protein that is neither a laminin nor a laminin fragment,
(B) coating the surface to be in contact with cells with the coating solution, and
(C) drying the coating solution applied in step (B).

5. A method for culturing mammalian cells, comprising placing the mammalian cells in the cell culture vessel according to claim 1, and culturing the mammalian cells.

6. The method according to claim 5, wherein the mammalian cells are ES cells, iPS cells, somatic stem cells or cells differentiated therefrom.

* * * * *

SEQUENCE LISTING

```
<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
atgatgatga agcttatcga taccgt                                          26

<210> SEQ ID NO 2
<211> LENGTH: 26
```

```
<212> TYPE: DNA
<213> ORGANISM: Artificial Sequence
<220> FEATURE:
<223> OTHER INFORMATION: Primer

<400> SEQUENCE: 2
catcatcatg atatcgaatt cctgca                                          26

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
atcatatgga taaagcttat cgataccgt                                       29

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
gtgccagatt atgcagatat cgaattcct                                       29

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
atccttgtaa tcaagcttat cgataccgt                                       29

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
gctgccgagg atgctgctgg ccagg                                           25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ctaggcagga tgccgggcgg gctga                                           25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
```
cttcagcata gtgctgctga cattg                                              25

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ttacaagcat gtgctataca cagcaac                                            27

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
aatgacattc tcaacaacct gaaag                                              25

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ctagggcttt tcaatggacg gggtg                                              25

<210> SEQ ID NO 12
<211> LENGTH: 15
<212> TYPE: PRT
<213> ORGANISM: Artificial Sequence
<220> FEATURE:
<223> OTHER INFORMATION: linker peptide

<400> SEQUENCE: 12

Asp Ala Glu Asp Ser Lys Leu Leu Pro Glu Pro Arg Ala Phe Pro
1               5                   10                  15

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
cctcaagcgg ctgaacacga caggcg                                             26

<210> SEQ ID NO 14
<211> LENGTH: 70
<212> TYPE: DNA
<213> ORGANISM: Artificial Sequence
<220> FEATURE:
<223> OTHER INFORMATION: Primer

<400> SEQUENCE: 14
atatggatcc tggaaaagcc cggggctctg caagagctt gctgtcctct gcatcaggcc        60
ccaggcccgg                                                               70

<210> SEQ ID NO 15

```
<211> LENGTH: 44
<212> TYPE: DNA
<213> ORGANISM: Artificial Sequence
<220> FEATURE:
<223> OTHER INFORMATION: Primer

<400> SEQUENCE: 15
atatatatgg atccgggctg agggcatacg atggcttgtc tctg            44

<210> SEQ ID NO 16
<211> LENGTH: 61
<212> TYPE: DNA
<213> ORGANISM: Artificial Sequence
<220> FEATURE:
<223> OTHER INFORMATION: Primer

<400> SEQUENCE: 16
atatatatgc ggccgcctaa tgatgatgat gatgatgtgg gaactggggc actgtgccca   60
g                                                                  61
```